(12) United States Patent
Ito et al.

(10) Patent No.: US 12,171,396 B2
(45) Date of Patent: Dec. 24, 2024

(54) ENDOSCOPE APPARATUS, OPERATING METHOD OF ENDOSCOPE APPARATUS, AND INFORMATION STORAGE MEDIUM

(71) Applicant: OLYMPUS CORPORATION, Tokyo (JP)

(72) Inventors: Takeshi Ito, Hino (JP); Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 961 days.

(21) Appl. No.: 17/133,873

(22) Filed: Dec. 24, 2020

(65) Prior Publication Data
US 2021/0145248 A1    May 20, 2021

Related U.S. Application Data

(63) Continuation of application No. PCT/JP2018/026076, filed on Jul. 10, 2018.

(51) Int. Cl.
*A61B 1/00* (2006.01)
*A61B 1/06* (2006.01)

(52) U.S. Cl.
CPC .... *A61B 1/000094* (2022.02); *A61B 1/00006* (2013.01); *A61B 1/00045* (2013.01);
(Continued)

(58) Field of Classification Search
CPC ........ A61B 1/000094; A61B 1/000095; A61B 1/0005; A61B 1/0638; A61B 1/0655
See application file for complete search history.

(56) References Cited

U.S. PATENT DOCUMENTS 9,801,531 B2    10/2017 Morita et al.
10,674,892 B2    6/2020 Kaku
(Continued)

FOREIGN PATENT DOCUMENTS

JP    2011-27997 A    2/2011
JP    2012-5807 A    1/2012
(Continued)

OTHER PUBLICATIONS

International Search Report received in International application No. PCT/JP2018/026076 dated Sep. 25, 2018, 2 pages.

*Primary Examiner* — Aaron B Fairchild
*Assistant Examiner* — Stephen Floyd London
(74) *Attorney, Agent, or Firm* — Scully, Scott, Murphy & Presser, P.C.

(57) ABSTRACT

An endoscope apparatus includes: an imaging device; a light source device; an illumination light control circuit; a first processing circuit; and a second processing circuit. The light source device emits first support illumination light in a first time period. The first processing circuit acquires a first support image obtained with the first support illumination light. The second processing circuit extracts first diagnosis support information on the basis of the first support image. The light source device emits second support illumination light being as a result of dimming control on the basis of the first diagnosis support information in a second time period. The first processing circuit acquires a second support image with the second support illumination light. The second processing circuit acquires support display information on the basis of the second support image. The first processing circuit executes image processing, based on the support display information, on the display image.

18 Claims, 10 Drawing Sheets

(52) U.S. Cl.
CPC .......... *A61B 1/0638* (2013.01); *A61B 1/0655* (2022.02); *A61B 1/000096* (2022.02)

(56) References Cited

U.S. PATENT DOCUMENTS

| | | | |
|---|---|---|---|
| 2008/0232131 A1* | 9/2008 | Suda | A61B 1/0655 362/574 |
| 2011/0021874 A1 | 1/2011 | Ogawa | |
| 2011/0071352 A1* | 3/2011 | Ozawa | A61B 1/0653 600/109 |
| 2012/0190922 A1 | 7/2012 | Kaku | |
| 2013/0184530 A1* | 7/2013 | On | A61B 1/00181 600/168 |
| 2016/0198076 A1* | 7/2016 | Fujimoto | H04N 23/673 348/68 |
| 2018/0008134 A1 | 1/2018 | Morita et al. | |
| 2018/0249889 A1* | 9/2018 | Imai | A61B 1/0655 |
| 2019/0087970 A1* | 3/2019 | Endo | A61B 1/000094 |
| 2019/0328206 A1 | 10/2019 | Muramatsu et al. | |
| 2020/0069160 A1* | 3/2020 | Oosake | A61B 1/000094 |

FOREIGN PATENT DOCUMENTS

| | | |
|---|---|---|
| JP | 2012152279 A | 8/2012 |
| JP | 2012-245161 A | 12/2012 |
| JP | 2013000176 A | 1/2013 |
| JP | 2016-144626 A | 8/2016 |
| WO | 2018003263 A1 | 1/2018 |

* cited by examiner

ENDOSCOPE APPARATUS, OPERATING METHOD OF ENDOSCOPE APPARATUS, AND INFORMATION STORAGE MEDIUM

CROSS REFERENCE TO RELATED APPLICATION

This application is a continuation of International Patent Application No. PCT/JP2018/026076, having an international filing date of Jul. 10, 2018, which designated the United States, the entirety of which is incorporated herein by reference.

BACKGROUND

An endoscope apparatus having a diagnosis support function has been known. An example of diagnosis support has proposed a function to extract a lesion from an image by artificial intelligence (AI) and present the lesion. For example, Japanese Unexamined Patent Application Publication No. 2016-144626 proposes an endoscope image processing device that calculates diagnosis support parameters on the basis of blood vessel information about an observation target object. In Japanese Unexamined Patent Application Publication No. 2016-144626, the endoscope image processing device supports diagnosis by extracting the blood vessel information from a special light image and presenting the special light image to an observer. In addition, Japanese Unexamined Patent Application Publication No. 2012-152279 discloses a method of matching a vascular pattern acquired from a special light image with a vascular pattern stored in advance, and providing diagnosis support on the basis of a matching result. In Japanese Unexamined Patent Application Publication No. 2012-152279, if the matching result indicates a match, a display prompts a user to change an imaging mode or an observation mode.

Further in an endoscope apparatus, dimming control has been known as an example of illumination light control. The dimming control controls brightness of illumination light on the basis of brightness of a display image, and thereby adjusts the brightness of the display image to appropriate brightness. For example, Japanese Unexamined Patent Application Publication No. 2012-245161 discloses a method of setting a region of interest to a captured image, and performing dimming control of a light quantity of illumination light on the basis of an image of the region of interest. In Japanese Unexamined Patent Application Publication No. 2012-245161, the captured image is displayed on a display section. That is, the dimming control is applied to the brightness of a display image.

SUMMARY

According to one aspect of the disclosure, there is provided an endoscope apparatus comprising:
an imaging device that captures an image of an object;
a light source device that emits display illumination light and support illumination light as illumination light onto the object;
an illumination light control circuit that controls the illumination light;
a first processing circuit that acquires a display image on the basis of an image signal obtained with the display illumination light and acquires a support image on the basis of an image signal obtained with the support illumination light; and
a second processing circuit that extracts diagnosis support information on the basis of the support image,
wherein
the illumination light control circuit causes the light source device to emit first support illumination light in a first time period,
the first processing circuit acquires a first support image on the basis of an image signal obtained with the first support illumination light,
the second processing circuit extracts first diagnosis support information to be used for dimming control, on the basis of the first support image,
the illumination light control circuit causes the light source device to emit second support illumination light in a second time period, the second support illumination light being as a result of the dimming control on the basis of the first diagnosis support information,
the first processing circuit acquires a second support image on the basis of an image signal obtained with the second support illumination light,
the second processing circuit acquires second diagnosis support information as support display information, on the basis of the second support image,
the first processing circuit executes image processing, based on the second diagnosis support information, on the display image, and outputs the display image as a result of the image processing to a display section.

According to another aspect of the disclosure, there is provided an endoscope apparatus, comprising:
an imaging device that captures an image of an object;
a light source device that emits first to k-th illumination light having different light quantities onto the object, where k is an integer of two or greater;
a first processing circuit that acquires first to k-th candidate images respectively corresponding to the first to k-th illumination light on the basis of an image signal from the imaging device; and
a second processing circuit,
wherein
the first processing circuit acquires a display image on the basis of the first to k-th candidate images, and outputs the first to k-th candidate images to the second processing circuit,
the second processing circuit extracts diagnosis support information on the basis of an image selected from the first to k-th candidate images, and re-selects an image from the first to k-th candidate images on the basis of the diagnosis support information.

According to another aspect of the disclosure, there is provided an operating method of an endoscope apparatus, the method comprising:
capturing an image of an object;
emitting display illumination light and support illumination light as illumination light onto the object;
controlling the illumination light;
acquiring a display image on the basis of an image signal obtained with the display illumination light, and acquiring a support image on the basis of an image signal obtained with the support illumination light;
extracting diagnosis support information on the basis of the support image;
emitting first support illumination light in a first time period;
acquiring a first support image on the basis of an image signal obtained with the first support illumination light;

extracting first diagnosis support information to be used for dimming control, on the basis of the first support image;
emitting second support illumination light in a second time period, the second support illumination light being as a result of the dimming control on the basis of the first diagnosis support information;
acquiring a second support image on the basis of an image signal obtained with the second support illumination light;
acquiring second diagnosis support information as support display information on the basis of the second support image; and
executing image processing, based on the second diagnosis support information, on the display image, and outputting the display image as a result of the image processing.

According to another aspect of the disclosure, there is provided a non-transitory information storage medium storing a program, the program causing a computer to execute steps comprising:
capturing an image of an object;
emitting display illumination light and support illumination light as illumination light onto the object;
controlling the illumination light;
acquiring a display image on the basis of an image signal obtained with the display illumination light, and acquiring a support image on the basis of an image signal obtained with the support illumination light;
extracting diagnosis support information on the basis of the support image;
emitting first support illumination light in a first time period;
acquiring a first support image on the basis of an image signal obtained with the first support illumination light;
extracting first diagnosis support information to be used for dimming control on the basis of the first support image;
emitting second support illumination light in a second time period, the second support illumination light being as a result of the dimming control on the basis of the first diagnosis support information;
acquiring a second support image on the basis of an image signal obtained with the second support illumination light;
acquiring second diagnosis support information as support display information on the basis of the second support image; and
executing image processing, based on the second diagnosis support information, on the display image, and outputting the display image as a result of the image processing.

DESCRIPTION OF EXEMPLARY EMBODIMENTS

Figure 1:
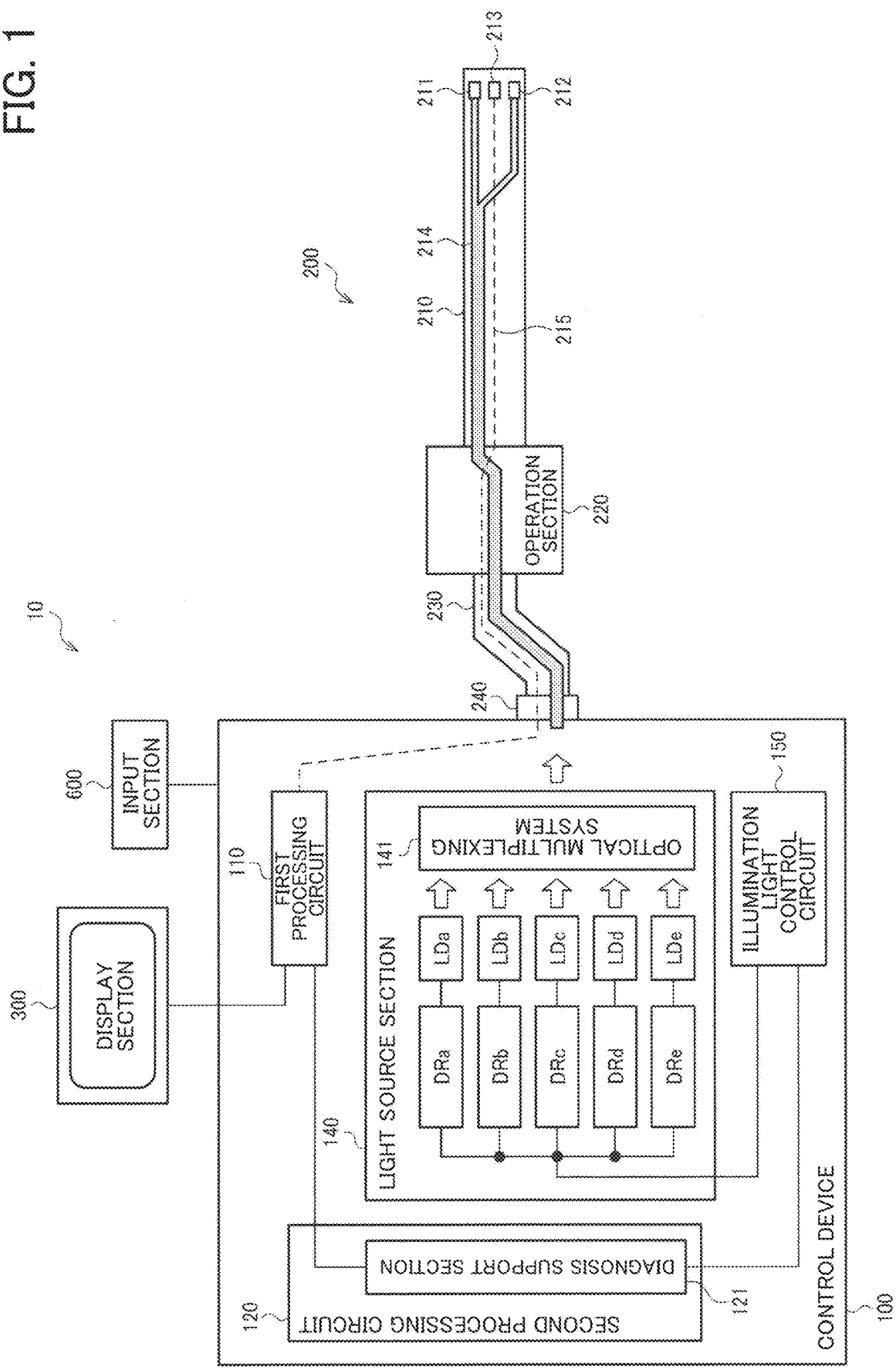
FIG. 1 illustrates a configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 is configuration example of an endoscope apparatus 10. The following description is directed to an example of a medical endoscope for digestive organs, but the scope of the present disclosure is not limited thereto. That is, the endoscope mentioned in the present specification generally covers an apparatus provided with an insertion section for observing internal surfaces of concave portions of various observation target objects. For example, the endoscope as mentioned herein is a medical endoscope for examination of a living body, or an industrial endoscope.

The endoscope apparatus 10 illustrated in FIG. 1 includes a control device 100, a scope section 200, a display section 300, and an input section 600. Note that the control device 100 is also referred to as a main section. The scope section 200 is also referred to as a scope, an imaging section, or an imaging device. The display section 300 is also referred to as a display or a display device. The input section 600 is also referred to as an input device or an operation device.

First, a configuration of the endoscope apparatus 10 will be described.

The scope section 200 is composed of an insertion section 210, an operation section 220, a connection cable 230, and a connector 240. The insertion section 210 has flexibility and can be inserted into a body cavity of the living body. The body cavity of the living body corresponds to an object in the present embodiment. The object is also referred to as an observation target or an observation target object. Note that FIG. 1 does not illustrate the object. An operator such as a doctor holds the operation section 220 and operates the endoscope apparatus 10 by means of the operation section 220. The connection cable 230 is a flexible cable to connect the control device 100 and the scope section 200. The connector 240 is arranged at one end of the connection cable 230 and enables attachment and detachment between the control device 100 and the scope section 200.

Two illumination lenses 211 and 212 that emit illumination light onto the object and an imaging unit 213 that receives illumination light reflected or scattered on the surface of the object and thereby captures an image are arranged at the distal end of the insertion section 210.

A light guiding path 214 is arranged in the scope section 200. The control device 100 is provided with a light source section 140, and illumination light emitted from the light source section 140 is guided to the illumination lenses 211 and 212 by the light guiding path 214. The light guiding path 214 is an optical fiber bundle, which extends from the connector 240, via the connection cable 230 and through the operation section 220, to the illumination lenses 211 and 212. The light guiding path 214 is a single bundle on the connector 240 side, and bifurcates in the insertion section 210 to be optically connected to the two illumination lenses 211 and 212.

The illumination lenses 211 and 212 widen illumination light guided by the optical fiber bundle to have a desired radiation angle. Each of the illumination lenses 211 and 212 is an illumination optical system composed of a single lens or a plurality of lenses.

The imaging unit 213 includes an imaging optical system and an image sensor. In the present embodiments, the image sensor is a complementary metal-oxide semiconductor (CMOS) imager, to which a red/green/blue (RGB) color filter in a Bayer's arrangement is mounted. That is, the image sensor is an image sensor of a primary color filter type having an R pixel, a G pixel, and a B pixel.

In addition, the scope section 200 is provided with an image signal line 215, which transmits image signals of an image captured by the imaging unit 213 to the control device 100. The image signal line 215 is arranged in the insertion section 210, the operation section 220, and the connection cable 230, and is electrically connected to the control device 100 via the connector 240. Note that the image signal line 215 may be an optical fiber for optical communication or the like.

The control device 100 includes: the light source section 140 that emits illumination light; an illumination light control circuit 150 that controls a light quantity, an emission timing, etc. of illumination light; a first processing circuit 110 that performs image processing on image signals from the imaging unit 213; and a second processing circuit 120 that generates diagnosis support information on the basis of an image output from the first processing circuit 110. Note that the light source section 140 is also referred to as a light source device. In addition, the first processing circuit 110 is also referred to as an image processing circuit.

For example, each circuit of the first processing circuit 110, the second processing circuit 120, and the illumination light control circuit 150 is implemented by an individual integrated circuit device. For example, each circuit is a processor, an application-specific integrated circuit (ASIC), or the like. In a case where each circuit is implemented by the processor, the processor executes a program describing operations of the circuit, thereby implementing the operations of the circuit. The program is, for example, stored in a memory (not illustrated). Note that two circuits freely selected out of the first processing circuit 110, the second processing circuit 120, and the illumination light control circuit 150, or all of the three circuits may be integrated as one integrated circuit device. In addition, the program described above can be stored, for example, in a computer-readable, non-transitory information storage medium. The information storage medium can be implemented by, for example, an optical disk, a memory card, a hard disk drive (HDD), a semiconductor memory, or the like. The semiconductor memory is, for example, a read-only memory (ROM) or a non-volatile memory.

The light source section 140 includes a plurality of light sources LDa to LDe, drive circuits DRa to DRe that drive the respective light sources LDa to LDe, and an optical multiplexing system 141 that multiplexes light emitted from the light sources LDa to LDe.

Each of the light sources LDa to LDe is a semiconductor laser element. In this case, illumination light is laser light. Alternatively, each of the light sources LDa to LDe may be a light emitting diode (LED). For example, an LED that emits narrowband light having a wavelength band of about several tens of nanometers can be adopted. However, the illumination light is not limited to the narrowband light, and may be illumination light having an appropriate band in accordance with, for example, viewability of a display image or a method of extracting support information. Note that the following description is given of an example where each of the light sources LDa to LDe is a semiconductor laser element.

Figure 2:
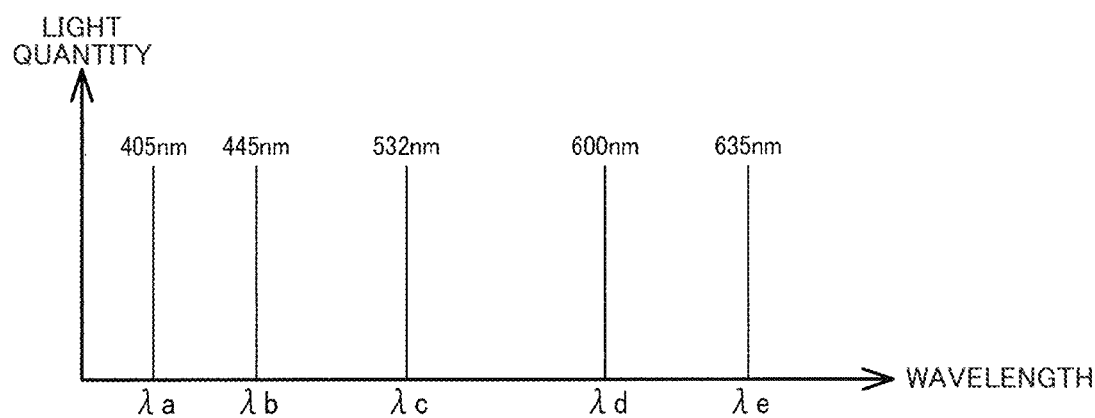
FIG. 2 illustrates an example of laser light emitted from a light source.

FIG. 2 illustrates an example of laser light emitted from the light sources LDa to LDe. As illustrated in FIG. 2, the light source LDa emits blue-violet laser light having a wavelength $\lambda a$ of 405 nm. The light source LDb emits blue laser light having a wavelength $\lambda b$ of 445 nm. The light source LDc emits green laser light having a wavelength $\lambda c$ of 532 nm. The light source LDd emits orange laser light having a wavelength $\lambda d$ of 600 nm. The light source LDe emits red laser light having a wavelength $\lambda e$ of 635 nm. A quantity of light emitted from each light source, being substantially in the same range in FIG. 2, is controlled by the illumination light control circuit 150.

As illustrated in FIG. 1, the drive circuits DRa, DRb, DRc, DRd, and DRe are electrically connected to the light sources LDa, LDb, LDc, LDd, and LDe, respectively. The light sources LDa to LDe generate laser light by power supplied from the drive circuits DRa to DRe, respectively.

The drive circuits DRa to DRe are electrically connected to the illumination light control circuit 150. The illumination light control circuit 150 controls the light sources LDa to LDe by transmitting control signals of a light quantity, an emission timing, etc. of laser light to the drive circuits DRa to DRe, respectively. Each of the light sources LDa to LDe can thus emit laser light in an independent laser light quantity and at an independent emission timing from the others. That is, the light sources LDa to LDe can be turned on and off independently of one another.

Laser light emitted from the light sources LDa to LDe is incident on the optical multiplexing system 141. A commonly used multiplexing optical technology can be applied to the optical multiplexing system 141. For example, the optical multiplexing system 141 is a spatial optical system that combines a plurality of dichroic mirrors or the like, or an optical combiner in which end surfaces of a plurality of optical fibers are connected to an end surface of one optical fiber.

Laser light emitted from the light sources LDa to LDe is multiplexed by the optical multiplexing system 141. The multiplexed laser light is emitted from one emission end toward an incident end of the light guiding path 214 arranged in the connector 240. Laser light incident on the incident end of a light waveguide path is guided by the light guiding path 214 to the illumination lenses 211 and 212 at the distal end of the insertion section 210, widened to have a desired radiation angle by the illumination lenses 211 and 212, and emitted toward the object.

The illumination light control circuit 150 controls the light quantities of the light sources LDa to LDe, independently or in coordination, via the drive circuits DRa to DRe. An emission timing of each laser light in the present embodiments will be described later.

The first processing circuit 110 performs various kinds of image processing on the basis of image signals transmitted from the imaging unit 213 via the image signal line 215. Specifically, the first processing circuit 110 generates a display image from image signals and outputs the display image to the display section 300. In addition, the first processing circuit 110 generates a support image from image signals and outputs the support image to the second processing circuit 120. Furthermore, the first processing circuit 110 receives diagnosis support information from the second processing circuit 120, adds display information corresponding to the diagnosis support information to the display image, and transmits the display image to the display section 300. The display information added to the display image is hereinafter referred to as support display information. For example, the support display information is information indicating a position or boundary of a portion of interest, and corresponds to, for example, a frame border, highlighting, an arrow, or the like added to the portion of interest. Alternatively, the support display information is information indicating a type or status of the portion of interest, and corresponds to, for example, characters or the like representing the type or the status.

The second processing circuit 120 includes a diagnosis support section 121. The diagnosis support section 121 is, for example, artificial intelligence (AI). That is, the diagnosis support section 121 extracts diagnosis support information from an input support image by AI processing, and transmits the diagnosis support information to the first processing circuit 110. Various kinds of image recognition methods or machine learning methods can be adopted to the AI processing. Machine learning is processing to perform various kinds of inferences on the basis of results of learning. Typical examples of AI include, but are not limited thereto, a neural network. Various kinds of known machine learning methods can be adopted to the AI in the present embodiments.

The connector 240 enables attachment and detachment of the image signal line 215, the light guiding path 214, and a power line (not illustrated) which supplies power to the imaging unit 213, electrically or optically with respect to the control device 100. Besides, the connector 240 has typical functions that come with a connector of an endoscope apparatus for making the control device 100 and the scope section 200 attachable and detachable with respect to each other. For example, the connector 240 may include an air supply pipe, a water supply pipe, or the like. In addition, the connector 240 may include a signal line to communicate information about the scope section 200 between the scope section 200 and the control device 100. The information about the scope section 200 is, for example, a type of an image sensor, an upper-limit value of a light quantity, and the like. The connector 240 may also include a power line for supplying power to an electric circuit mounted in the scope section 200. In addition, the connector 240 may include a signal line for inputting and outputting signals between the electric circuit mounted in the scope section 200 and the control device 100.

The display section 300 displays an object image as a result of image processing by the first processing circuit 110. The display section 300 is any of various kinds of commonly used display devices and is, for example, a liquid crystal monitor or the like. The display section 300 and the control device 100 are electrically connected to each other by electric wiring. Image signals output from the first processing circuit 110 are transmitted to the display section 300 by this electric wiring.

Next, basic operations of the endoscope apparatus 1 will be described. Note that the following description omits operations common to those of a typical endoscope, and focuses on features related to the present disclosure.

The diagnosis support section 121 analyzes whether or not a portion of interest is present in an image. When detecting a portion of interest, the diagnosis support section 121 extracts information regarding the portion of interest from the image, and outputs the information as diagnosis support information to the first processing circuit 110 and the illumination light control circuit 150. The diagnosis support information output to the illumination light control circuit 150 is necessary to optimize the brightness, the wavelength, or the light quantity ratio of illumination light. For example, the diagnosis support information is information indicating a position of the portion of interest in the image and brightness of the image at the position. The illumination light control circuit 150 adjusts a light quantity of illumination light on the basis of the brightness of the image at the position of the portion of interest, and thereby adjusts the brightness of the image at the position of the portion of interest to appropriate brightness. The brightness of the image is, for example, luminance of the image. The appropriate brightness means that the brightness is appropriate for the diagnosis support section 121 to extract information regarding the portion of interest. In other words, the dimming herein does not necessarily improve viewability for humans.

Illumination light controlled on the basis of the diagnosis support information illuminates the object, whose image is captured by the imaging unit 213. The diagnosis support section 121 re-extracts diagnosis support information on the basis of a support image obtained from the image signals. That is, while the portion of interest is extracted in the extraction processing before the illumination light control, the diagnosis support section 121 re-extracts the diagnosis support information regarding the portion of interest from the support image after the illumination light control. In the support image after the illumination light control, information associated with support information about the portion of interest has increased. For example, the support image shows blood vessels with a higher contrast or has a higher resolution. Eventually, the diagnosis support section 121 can re-extract the diagnosis support information regarding the portion of interest more accurately.

The support image from which the diagnosis support information is extracted and a display image to be displayed on the display section 300 are different images. In this case, illumination light control for the display image is different from illumination light control for the support image. For example, while dimming control for the display image is performed to achieve appropriate brightness over the entire display image, dimming control for the support image is performed to achieve appropriate brightness at the portion of interest.

The support image mentioned herein is not displayed on the display section 300. That is, the support image only needs to be an image acquired for diagnosis support aside from the display image. The support image and the display image are not necessarily images of different types or in different combinations, but may be images of the same type or in the same combination. For example, in an example in FIG. 4 to be described later, the display image is generated from a B image, a G image, an A image, and an R image, and the support image utilizes a V image and the G image. This is a case where the display image and the support image are images in different combinations. As an alternative example, both the display image and the support image may be white light images. This is a case where the display image and the support image are images of the same type, and a white light display image and a white light support image are provided separately. Illumination light control for the white light display image and illumination light control for the white light support image are performed independently of each other.

Note that the description has been given of the case where the illumination light control circuit 150 controls illumination light on the basis of the diagnosis support information, but the scope of the present disclosure is not limited thereto. For example, the first processing circuit 110 may determine, on the basis of the diagnosis support information, at which wavelength the image to be output to the second processing circuit 120 as the support image should be captured. Alternatively, the first processing circuit 110 may adjust brightness of the image at the position of the portion of interest to appropriate brightness by gain processing on the support image on the basis of the diagnosis support information, and may then output the adjusted support image to the second processing circuit 120. Further alternatively, the illumination light control performed by the illumination light control circuit 150 on the basis of the diagnosis support information may be combined with display control performed by the first processing circuit 110 on the basis of the diagnosis support information.

In accordance with the above-described embodiment, the endoscope apparatus 10 includes the imaging section, the illumination light control circuit 150, and the first processing circuit 110. The imaging section captures an image of the object. The light source section 140 emits display illumination light and support illumination light as illumination light onto the object. The illumination light control circuit 150 controls illumination light. The first processing circuit 110 acquires the display image on the basis of image signals obtained with the display illumination light, and acquires the support image on the basis of image signals obtained with the support illumination light. The first processing circuit 110 outputs the display image to the display section 300 and also outputs the support image to the second processing circuit 120. The illumination light control circuit 150 acquires the diagnosis support information. The diagnosis support information is extracted from the support image by the second processing circuit 120. The illumination light control circuit 150 controls the support illumination light on the basis of the diagnosis support information.

In FIG. 1, the imaging section corresponds to the imaging unit 213. Note that the second processing circuit 120 in the example of FIG. 1 is included in the endoscope apparatus 10, but instead the second processing circuit 120 may be arranged outside the endoscope apparatus 10 as will be described later with reference to FIG. 11. That is, the present disclosure can be applied to a case where the endoscope apparatus 10 does not include the second processing circuit 120.

The present embodiments perform feedback control of illumination light control on the basis of the diagnosis support information. Eventually, an image can be captured with illumination light appropriate for extracting the diagnosis support information. The present embodiments re-extract the diagnosis support information on the basis of the thus captured image, and can thereby extract the diagnosis support information more accurately. In addition, the present embodiments control support illumination light on the basis of the diagnosis support information, and captures the support image with the thus controlled support illumination light. That is, the illumination light control for the display image and the illumination light control for the support image can be performed separately. This enables appropriate illumination light control for the support image without affecting display quality.

For example, it is typical in an endoscopic apparatus by conventional technologies to set brightness of illumination light in consideration of brightness in the whole screen. Specifically, brightness of illumination light is set in accordance with any one of various photometry modes such as an average photometry mode of averaging brightness of the image with current illumination light in an observation region and a central-weighted photometry mode. In a case where the support information is extracted by AI or the like, a portion of interest is extracted from such an image, in which the portion of interest, depending on its position, is not necessarily captured under appropriate dimming control. Inappropriate light control may possibly decrease accuracy in extracting the portion of interest or may decrease accuracy in classifying the portion of interest. In contrast, the present embodiments can obtain an image having appropriate brightness for extracting the diagnosis support information, and can thereby classify the portion of interest more accurately. Note that the illumination light control is not limited to the dimming control, and may be control of a wavelength or a light quantity ratio of illumination light.

Further in the present embodiments, the first processing circuit 110 performs image processing on the display image on the basis of the diagnosis support information, and outputs the display image as a result of the image processing to the display section 300.

The resulting endoscope apparatus can provide an operator with the support display information, on the basis of and corresponding to the diagnosis support information extracted from the support image. At this time, the display image is under the illumination light control that is optimum for observation, while the support image acquired aside from the display image is under the illumination light control that is optimum for the AI processing. That is, the present embodiment can provide an image whose brightness makes the image easily viewable by the operator, and can add more accurate support display information to this image.

Further in the present embodiments, the illumination light control circuit 150 controls a light quantity of the display illumination light on the basis of the display image.

The present embodiments perform the illumination light control for the display image and the illumination light control for the support image independently of each other. As described above, the present embodiments enable the appropriate illumination light control for the support image without affecting display quality.

2. First Embodiment

Figure 3:
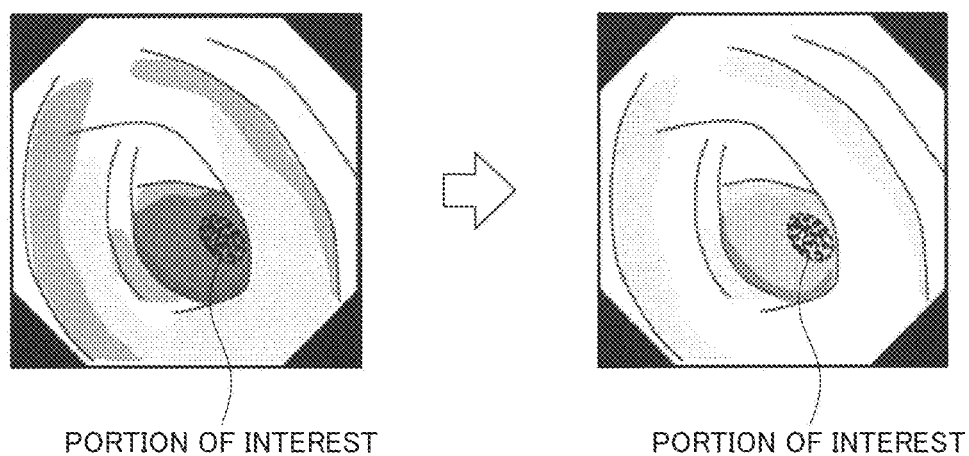
FIG. 3 shows illumination light control in accordance with a first embodiment.

FIG. 3 shows illumination light control in accordance with a first embodiment.

In the first embodiment, the endoscope apparatus 10 adjusts a light quantity of illumination light to provide an image of the portion of interest at appropriate brightness. This embodiment does not require special image processing, and thus does not need addition of a special member to a system.

FIG. 3 illustrates a large intestine as an example of an observation target. In the left drawing of FIG. 3, a portion of interest is on the far side of the intestinal tract. When the portion of interest is found on the far side of the body cavity, as illustrated, the portion of interest appears dark in an image. In such a case, the endoscope apparatus may not be able to acquire sufficient diagnosis support information regarding the portion of interest. That is, in an image analysis by the AI or the like, the AI or the like can detect the portion of interest, but cannot evaluate details of the portion of interest because the image of the portion of interest is dark. For example, in a case where the portion of interest is a lesion, the AI or the like cannot evaluate the detailed classification of the lesion, the detailed status of the lesion, or the like. As illustrated in the right drawing of FIG. 3, the endoscope apparatus 10 of the present embodiment increases a light quantity of illumination light to illuminate the portion of interest at optimum brightness, and captures an image of the object again with the illumination light. The endoscope apparatus 10 then causes the AI or the like to re-extract the portion of interest on the basis of the image captured after the light quantity is increased, and thus can determine whether or not the portion of interest is a lesion or can determine a detailed classification of the lesion. Although the periphery part of the image is brighter in the right drawing of FIG. 3, the brightness of the periphery part, where no portion of interest has been detected in the previous analysis, poses little problem for the purpose of extracting the diagnosis support information.

Note that the present embodiment sets a light quantity by calculating backward from the brightness of the image so as to provide the image of the portion of interest at optimum brightness, but the scope of the present disclosure is not limited thereto. For example, the present embodiment may optimize a light quantity by a lesion-weighted photometry mode to optimize the exposure of the lesion and re-acquire an image with the light quantity.

Figure 4:
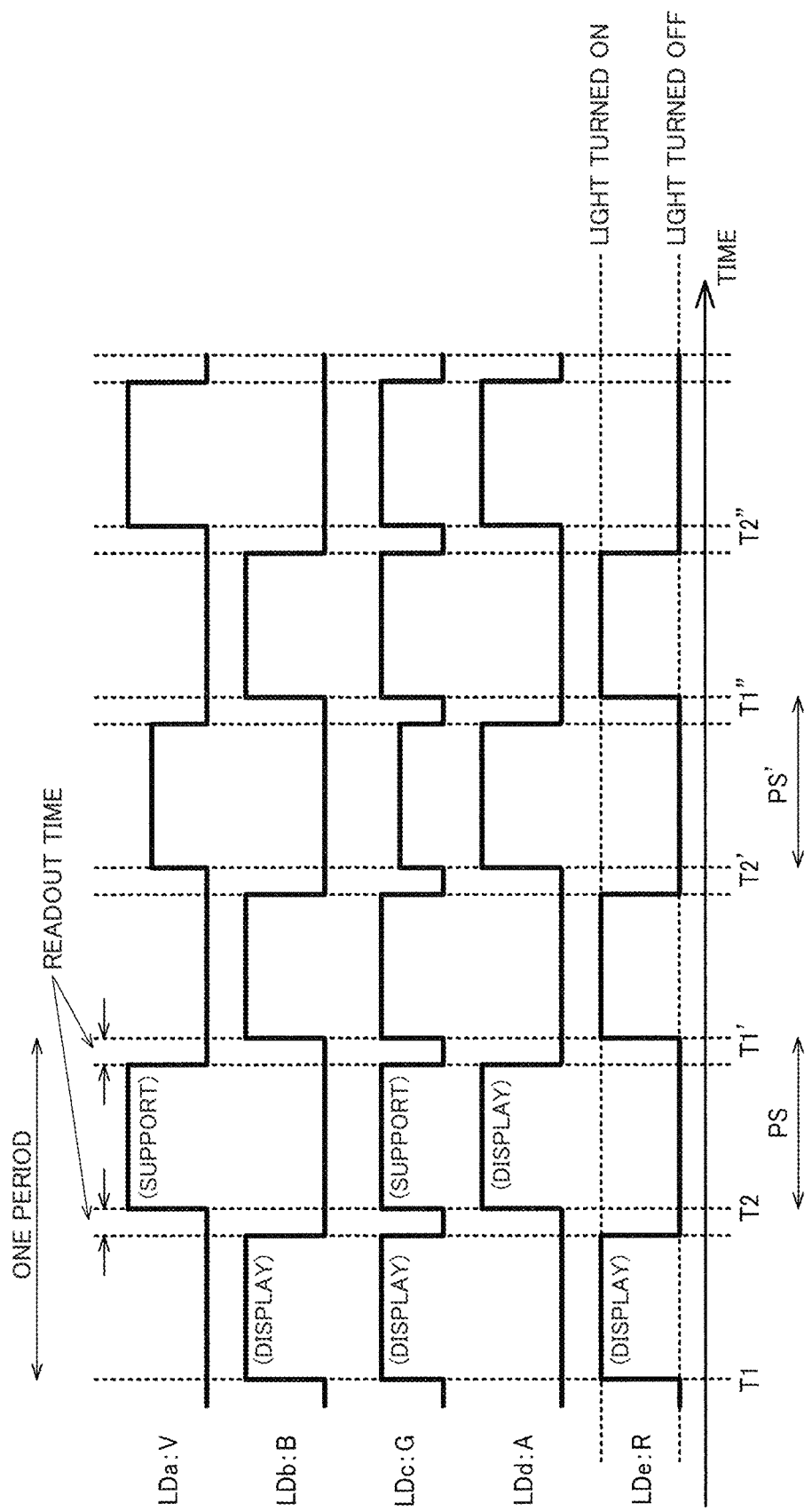
FIG. 4 illustrates an example of a light emission sequence in accordance with the first embodiment.

FIG. 4 illustrates an example of an emission sequence in accordance with the first embodiment. In FIG. 4, the abscissa axis represents time. FIG. 4 illustrates timings to turn on and off light at the light sources LDa, LDb, LDc, LDd, LDe, listed vertically from top to bottom. Timing is indicated by T1, T2, etc. In the following description, timing is indicated by abbreviations T1, T2, etc., without the term "timing".

As illustrated in FIG. 4, the light sources LDa to LDe are caused to emit light in a period of T1 to T1', during which the image sensor performs imaging operations twice. That is, one period includes two imaging frames.

In a time period from T1 to T2 excluding a readout time of the image sensor, the illumination light control circuit 150 causes the light sources LDb, LDc, and LDe to emit light. The image sensor is an RGB image sensor having a primary color filter. Thus, blue light from the light source LDb is detected by the B pixel, and consequently output as the B image. Similarly, green light from the light source LDc is detected by the G pixel, and output as the G image. Red light from the light source LDe is detected by the R pixel, and output as the R image. These pieces of image information are output from the image sensor in the readout time in which all the light sources LDa to LDe are turned off.

Subsequently, in the time period from T2' to T1 excluding the readout time of the image sensor, the illumination light control circuit 150 causes the light sources LDa, LDc, and LDd to emit light. Purple light from the light source LDa is detected by the B pixel, and consequently output as the V image. Similarly, green light from the light source LDc is detected by the G pixel, and output as the G image. Orange light from the light source LDd is detected by the R pixel, and consequently output as the A image. These pieces of image information are output from the image sensor in the readout time.

The first processing circuit 110 generates the display image from the B, G, and R images captured between T1 and T2, and the A image captured between T2 and T1'. Specifically, the first processing circuit 110 allocates a combined image composed of the R image and the A image to an R channel of the display image, allocates the B image to a B channel of the display image, and allocates the G image to a G channel of the display image. In addition, the first processing circuit 110 outputs the V image and the G image captured between T2 and T1' to the diagnosis support section 121 as the support image. The first processing circuit 110 may instead output a combined image composed of these V and G images to the diagnosis support section 121 as the support image.

The endoscope apparatus 10 of the present embodiment continuously repeats the operations in the one period described above. The dimming control is performed by repeating the following operations.

The illumination light control circuit 150 performs the dimming control of the light sources LDb, LDc, and LDe that emit light between T1' and T2' and the light source LDd that emits light between T2' and T1", on the basis of brightness of the display image acquired between T1 and T1'. That is, the dimming control in the current frame is performed on the basis of the display image in the previous frame. This dimming control is also referred to as display dimming control or first dimming control.

In addition, the illumination light control circuit 150 performs the dimming control of the light sources LDa and LDc that emit light between T2' and T1", on the basis of the support image acquired in the time period from T2 to T1' and also on the basis of the diagnosis support information extracted from the support image. That is, the dimming control in the current frame is performed on the basis of the support image and the diagnosis support information in the previous frame. This dimming control is also referred to as support dimming control or second dimming control.

Each of the display dimming control and the support dimming control is independently performed. For example, as illustrated in FIG. 4, light quantities of the light sources LDa and LDc that emit light between T2' and T1" are smaller than respective light quantities of the light sources LDa and LDc that emit light between T2 and T1'. This is a result of the support dimming control. In contrast, light quantities of the light sources LDb, LDc, and LDe that emit light between T1' and T2' are the same as respective light quantities of the light sources LDb, LDc, and LDe that emit light between T1 and T2. In addition, a light quantity of the light source LDd that emits light between T2' and T1" is the same as a light quantity of the light source LDd that emits light between T2 and T1'. This is a result of the display dimming control, which has determined to maintain the light quantity.

In accordance with the above-described embodiment, the illumination light control circuit 150 causes the light source section 140 to emit first support illumination light in a first time period. The first processing circuit 110 acquires a first support image on the basis of image signals obtained with the first support illumination light. The illumination light control circuit 150 acquires the diagnosis support information extracted by the second processing circuit 120 on the basis of the first support image. The illumination light control circuit 150 causes the light source section 140 to emit second support illumination light on the basis of the diagnosis support information in a second time period. The first processing circuit 110 acquires a second support image on the basis of image signals obtained with the second support illumination light. The first processing circuit 110 acquires the diagnosis support information re-extracted by the second processing circuit 120 on the basis of the second support image.

In the example of FIG. 4, the first time period corresponds to a time period PS from T2 to T1'. The second time period corresponds to a time period PS' from T2' to T1". The first support illumination light is light emitted from the light sources LDa and LDc in the time period PS. The second support illumination light is light emitted from the light sources LDa and LDc in the time period PS'.

The present embodiment extracts the diagnosis support information on the basis of the first support image captured with the first support illumination light, and controls the second support illumination light on the basis of the extracted diagnosis support information. The present embodiment then re-extracts the diagnosis support information on the basis of the second support image captured with the controlled second support illumination light. This enables feedback control of the support illumination light on the basis of the diagnosis support information, the feedback control being aside from the illumination light control for the display image.

In addition, the endoscope apparatus 10 in the present embodiment includes the second processing circuit 120. The second processing circuit 120 extracts, as the diagnosis support information, information about the portion of interest on the basis of the first support image, and re-extracts the diagnosis support information regarding the portion of interest on the basis of the information about the portion of interest and the second support image.

In a case where the portion of interest is detected, the present embodiment can re-extract more detailed diagnosis support information regarding the portion of interest. At this time, the present embodiment captures the support image with the illumination light as a result of the feedback control on the basis of the diagnosis support information, and re-extracts the diagnosis support information on the basis of the support image. That is, a region of interest detected before adjustment of illumination light is re-analyzed after the illumination light is optimally adjusted, so that the present embodiment can increase accuracy of the diagnosis support information regarding the region of interest.

Furthermore, in the present embodiment, the diagnosis support information includes information about the portion of interest included in the object. The illumination light control circuit 150 controls a light quantity of the support illumination light on the basis of brightness of the portion of interest in the support image. Specifically, as the information about the portion of interest, the diagnosis support information includes position information about the portion of interest and brightness information about the image of the portion of interest. The illumination light control circuit 150 controls a light quantity of the support illumination light on the basis of the diagnosis support information. Note that the present embodiment is not limited to a case of inputting the position information about the portion of interest and the brightness information about the image of the portion of interest to the illumination light control circuit 150. For example, the brightness information about the image of the portion of interest need not be input to the illumination light control circuit 150. In this case, the illumination light control circuit 150 may acquire the image of the portion of interest in the support image on the basis of the position information about the portion of interest, and may control a light quantity of the support illumination light on the basis of the brightness information about the acquired image of the portion of interest.

The present embodiment performs feedback control of brightness of the portion of interest in the image on the basis of the diagnosis support information. That is, the present embodiment can control brightness of the image of the detected portion of interest to appropriate brightness. The present embodiment can then re-extract the diagnosis support information regarding the portion of interest on the basis of the image of the portion of interest that has been controlled to have the appropriate brightness.

In the present embodiment, the illumination light control circuit 150 further performs control of approximating a luminance value at a predetermined region in an image to a target value by controlling a light quantity of illumination light. The predetermined region is a region including the portion of interest.

In the present embodiment, the illumination light control circuit 150 further assigns weights to the luminance value at the predetermined region and a luminance value at other regions, and then sets a light quantity target of illumination light on the basis of the weighted luminance values.

In addition, the present embodiment sets a light quantity target of illumination light on the basis of a difference between the luminance value at the predetermined region or the weighted luminance value and the target value.

Furthermore, the endoscope apparatus 10 in the present embodiment may have a plurality of observation modes. The plurality of observation modes includes, for example, a normal light observation mode, a narrow band imaging (NBI) observation mode, and a red band imaging (RBI) observation mode. The first processing circuit 110 acquires images in each of the observation modes. An image in the normal light observation mode is, for example, a white light image that combines the B image, the G image, the A image, and the R image. An image in the NBI observation mode is an NBI image that combines the V image and the G image. An image in the RBI observation mode is an RBI image that combines the G image, the A image, and the R image. The first processing circuit 110 selects the display image and the support image from the white light image, the NBI image, and the RBI image. For example, the first processing circuit 110 selects an image corresponding to an observation mode set by an operator as the display image, and selects other images as the support images.

3. Second Embodiment

A second embodiment performs gain processing on a captured image, and extracts diagnosis support information from the image as a result of the gain processing. The gain processing is gain-up or gain-down. The gain-up is also called sensitized development. The gain-down is also called desensitized development. This enables structuring of an image having optimized brightness of a portion of interest without acquiring an image again.

Figure 5:
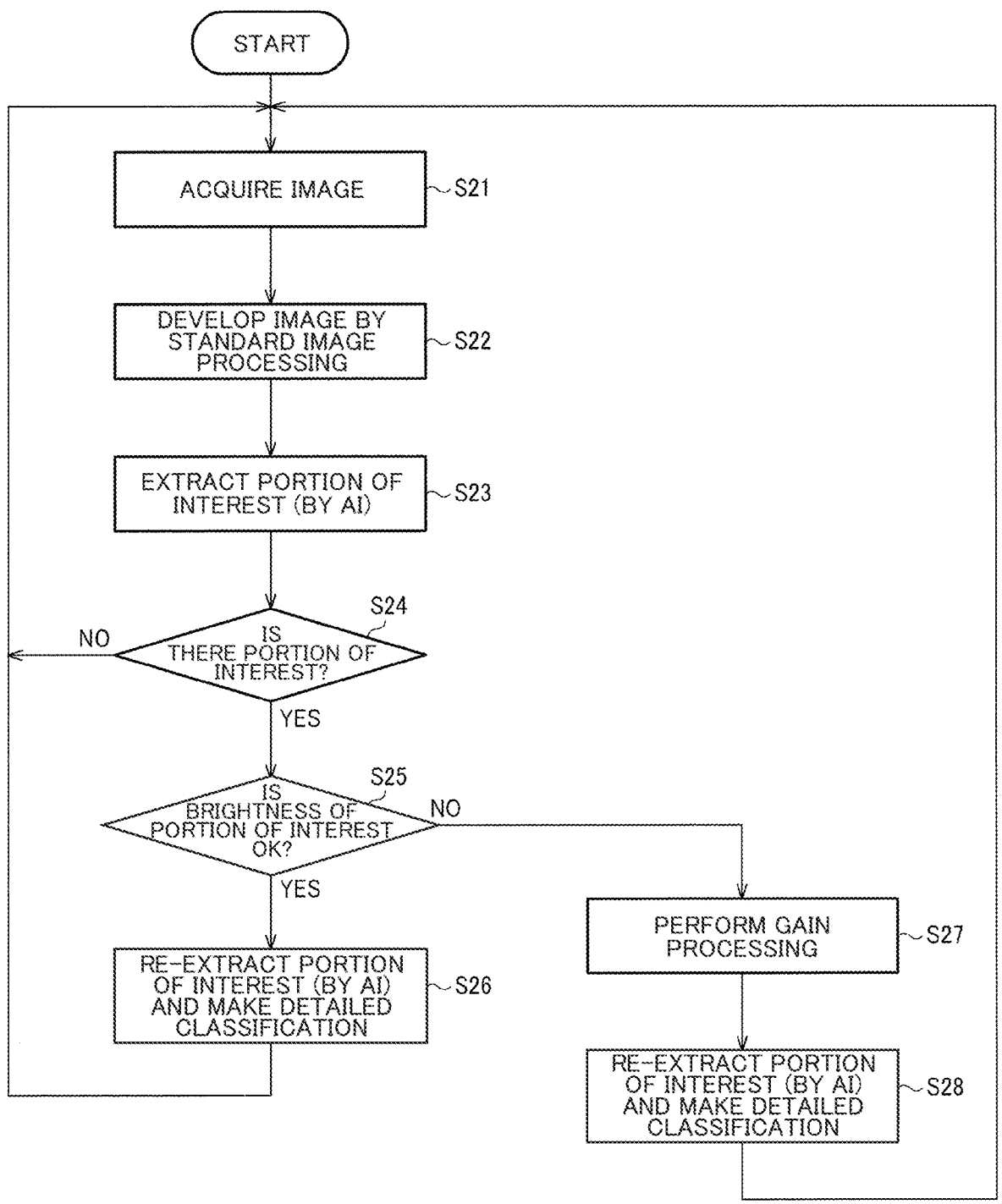
FIG. 5 is a flowchart describing operations of an endoscope apparatus in accordance with a second embodiment.

FIG. 5 is a flowchart describing operations of the endoscope apparatus 10 in accordance with the second embodiment.

To start with, the imaging unit 213 acquires an image in step S21. Subsequently, as indicated in step S22, the first processing circuit 110 develops the image by performing standard image processing, and outputs the image to the diagnosis support section 121. The standard image processing is typical development processing, and is, for example, development processing to generate a display image. The first processing circuit 110 outputs the developed image to the display section 300, which displays the image.

Turning next to step S23, the diagnosis support section 121 extracts a portion of interest from the image. That is, the diagnosis support section 121 determines whether or not a portion of interest is present in the image. If a portion of interest is present, the diagnosis support section 121 extracts diagnosis support information regarding the portion of interest.

Subsequently, as indicated in step S24, the second processing circuit 120 acquires information indicating whether or not the diagnosis support section 121 has detected a region of interest. If no attention area is present in the image, the processing returns to step S21. If a portion of interest is present in the image, the second processing circuit 120 determines whether or not brightness of the portion of interest in the image is appropriate, as indicated in step S25.

If the brightness of the portion of interest is appropriate in step S25, the diagnosis support section 121 re-extracts the portion of interest from the image and makes a detailed classification of the portion of interest, as indicated in step S26. After execution of step S26, the processing returns to step S21.

If the brightness of the portion of interest is not appropriate in step S25, the second processing circuit 120 performs gain processing on the image, as indicated in step S27. If determining that the brightness of the portion of interest is lower than appropriate brightness, the second processing circuit 120 gains up the image. On the other hand, if determining that the brightness of the portion of interest is higher than the appropriate brightness, the second processing circuit 120 gains down the image. Taking a gain of the standard image processing in step S22 as a reference, the gain-up is to make a gain higher than the reference, and the gain-down is to make a gain lower than the reference. The image as a result of the gain processing is input to the diagnosis support section 121.

Subsequently, as indicated in step S28, the diagnosis support section 121 re-extracts the portion of interest from the image as a result of the gain processing, and makes a detailed classification of the re-extracted portion of interest. After execution of step S28, the processing returns to step S21.

Figure 6:
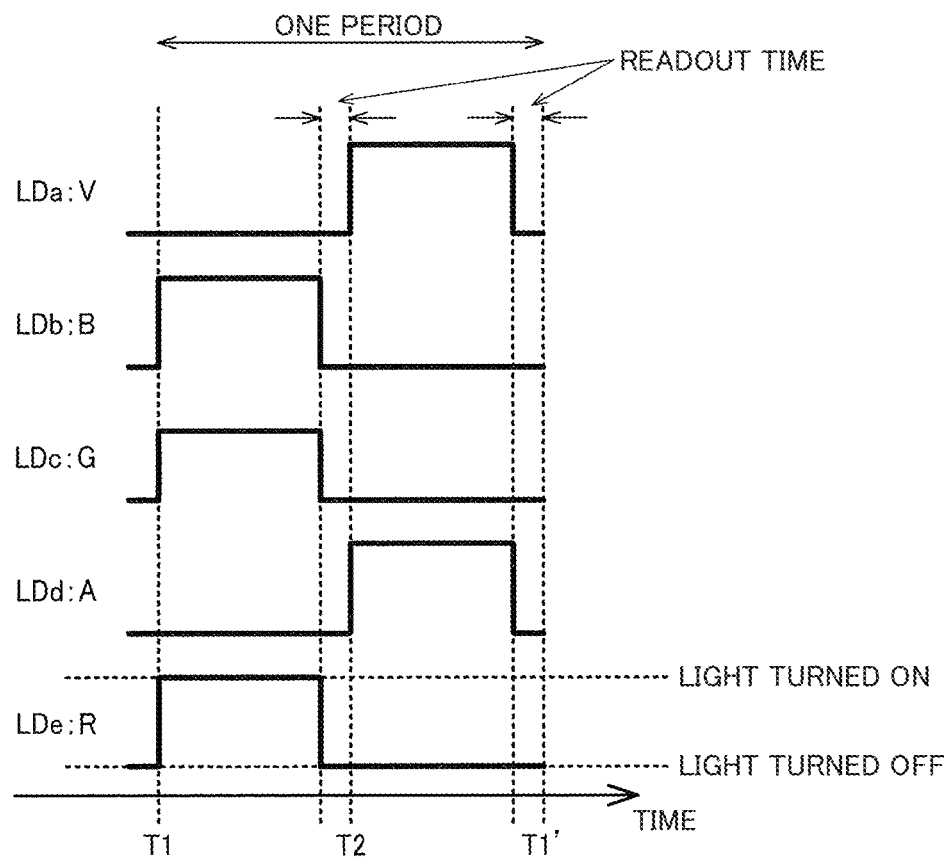
FIG. 6 illustrates an example of a light emission sequence in accordance with the second embodiment.

FIG. 6 illustrates an example of an emission sequence in accordance with the second embodiment.

In a time period from T1 to T2 excluding a readout time of the image sensor, the illumination light control circuit 150 causes the light sources LDb, LDc, and LDe to emit light. Subsequently, in a time period from T2 to T1' excluding a readout time of the image sensor, the illumination light control circuit 150 causes the light sources LDa and LDd to emit light. The V image, the B image, the G image, the A image, and the R images are obtained just as described with reference to FIG. 4. The first processing circuit 110 freely selects images from these five images, and generates a display image from the selected images. The kind of display image to be generated is set, for example, by an observation mode. The endoscope apparatus 10 continuously repeats the operations in the one period described above.

The second embodiment does not perform the support dimming control because the images as a result of the gain processing are input to the diagnosis support section 121. That is, the illumination light control circuit 150 performs display dimming control for the light sources LDa to LDe. More specifically, brightness of each of the V image, the B image, the G image, the A image, and the R image is controlled by the display dimming control. The first processing circuit 110 performs the gain processing on these images, and outputs the images as a result of the gain processing to the diagnosis support section 121. The first processing circuit 110 freely selects one or more images from these five images as support image(s). At this time, the first processing circuit 110 performs the gain processing on the image(s) selected as the support image(s), and outputs the image(s) as a result of the gain processing to the diagnosis support section 121.

While the light sources LDa to LDe are caused to emit light separately in two imaging frames in FIG. 6, the present embodiment is not limited thereto, and the light sources LDa to LDe may be caused to emit light in one imaging frame. In this case, one period of the emission sequence corresponds to one imaging frame. In addition, light emitted from the light sources LDa and LDb is detected by the B pixel, light emitted from the light source LDc is detected by the G pixel, and light emitted from the light sources LDd and LDe is detected by the R pixel. Thus obtained is a white light image.

In accordance with the above-described embodiment, the first processing circuit 110 outputs the display image to the display section and also outputs the support image to the second processing circuit 120. The second processing circuit 120 extracts the diagnosis support information from the support image, and performs gain adjustment on the support image on the basis of the diagnosis support information.

Furthermore, in the present embodiment, the second processing circuit 120 re-extracts the diagnosis support information on the basis of the support image as a result of the gain adjustment. The first processing circuit 110 performs the image processing on the display image on the basis of the diagnosis support information re-extracted by the second processing circuit 120.

The present embodiment performs the gain processing on the support image on the basis of the diagnosis support information, thereby performing feedback control of the brightness of the support image. The present embodiment can thus acquire an image having appropriate brightness for extracting the diagnosis support information. Then, the present embodiment re-extracts the diagnosis support information on the basis of the thus acquired image, and can thereby extract the diagnosis support information more accurately. In addition, this feedback control is performed independently of the dimming control for the display image. Hence, the present embodiment can provide an image whose brightness makes the image easily viewable by the operator, and can add more accurate support display information to this image. Furthermore, the second processing circuit 120 performs the feedback control, thereby eliminating the need for changing a conventional dimming control system or the like.

4. Third Embodiment

In a third embodiment, when a portion of interest is extracted, the endoscope apparatus 10 acquires an image having optimum brightness of the portion of interest between acquisition of one display image and acquisition of a next display image. This embodiment can thus re-extract the portion of interest on the basis of the image having the optimum brightness of the portion of interest, and can also provide a display image having natural brightness to the operator without being affected by the brightness of the portion of interest.

Figure 7:
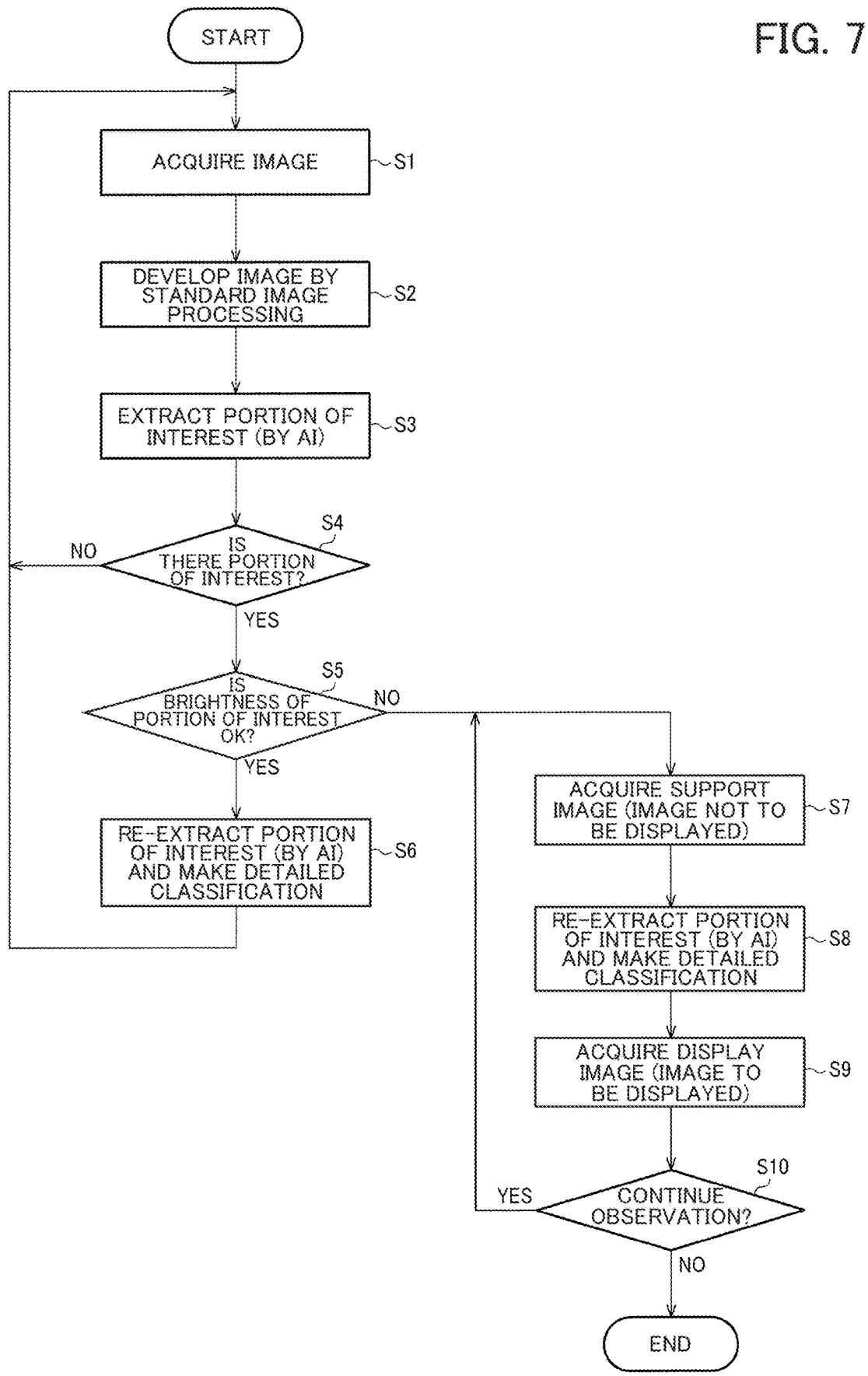
FIG. 7 is a flowchart describing operations of an endoscope apparatus in accordance with the third embodiment.

FIG. 7 is a flowchart describing operations of the endoscope apparatus 10 in accordance with the third embodiment. Steps S1 to S6 are the same as steps S21 to S26 in FIG. 5, and a description thereof is omitted.

In a case where the brightness of the portion of interest is not appropriate in step S5, the illumination light control circuit 150 causes emission of illumination light and the first processing circuit 110 acquires a support image, as indicated in step S7. The first processing circuit 110 outputs the acquired support image to the diagnosis support section 121. The illumination light mentioned herein is emitted aside from illumination light for acquiring the display image. That is, the support image is an image not to be displayed. If the second processing circuit 120 determines that the brightness of the portion of interest is lower than appropriate brightness, the illumination light control circuit 150 increases a light quantity of the illumination light. On the other hand, if the second processing circuit 120 determines that the brightness of the portion of interest is higher than the appropriate brightness, the illumination light control circuit 150 decreases the light quantity of the illumination light. For example, taking a light quantity at the timing of acquiring the image in step S1 as a reference, the illumination light control circuit 150 increases or decreases the light quantity relative to the reference.

Subsequently, as indicated in step S8, the diagnosis support section 121 re-extracts the portion of interest from the support image, and makes a detailed classification of the re-extracted portion of interest. Next in step S9, the illumination light control circuit 150 causes emission of illumination light, and the first processing circuit 110 acquires a display image. The first processing circuit 110 outputs the acquired display image to the display section 300. The illumination light mentioned herein is illumination light for acquiring the display image. In addition, the first processing circuit 110 develops an image by the standard image processing in a similar manner to step S2.

Subsequently, as indicated in step S10, the first processing circuit 110 determines whether or not to continue observation. For example, the first processing circuit 110 determines whether or not to continue observation on the basis of information input by the operator through the operation section 220 or the input section 600. If the observation is not to be continued, the processing ends. If the observation is to be continued, the processing returns to step S7.

As described above, if the brightness of the portion of interest in the image is not appropriate, the endoscope apparatus 10 acquires the display image and the support image alternately.

Figure 8:
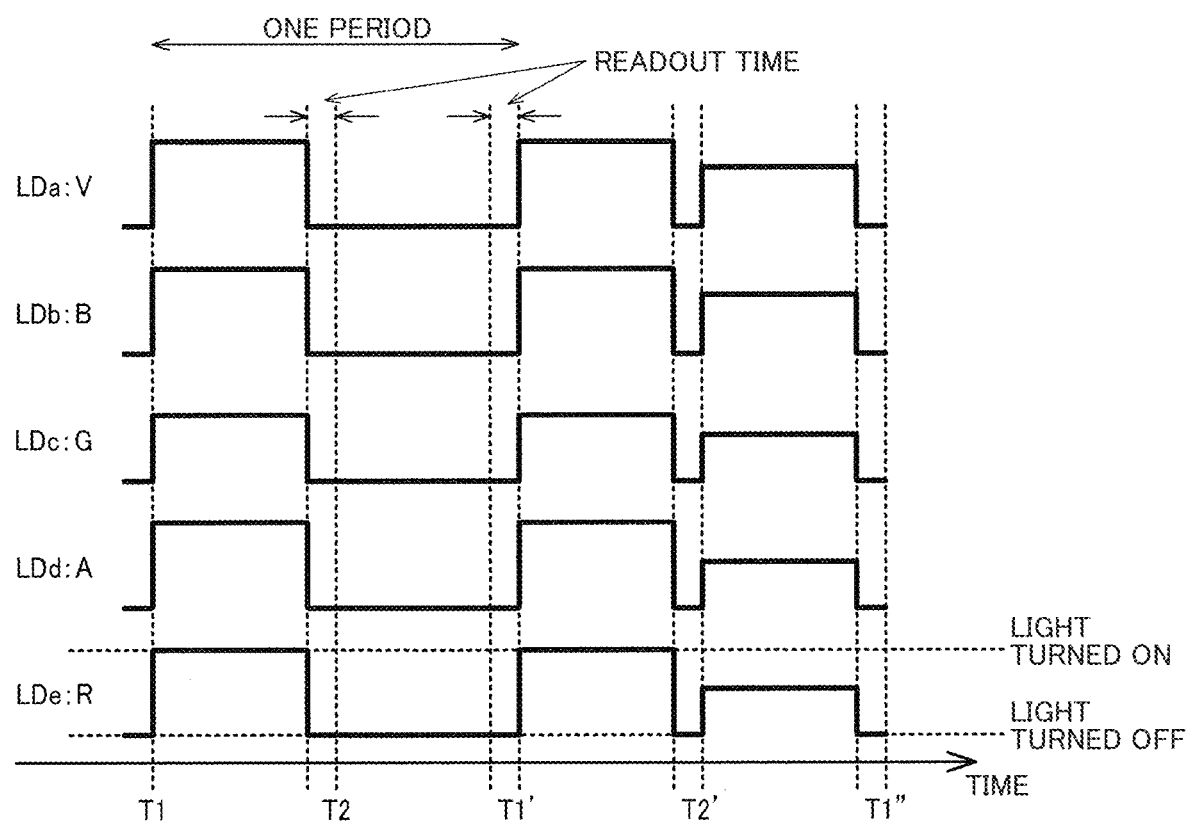
FIG. 8 illustrates an example of a light emission sequence in accordance with the third embodiment.

FIG. 8 illustrates an example of an emission sequence in accordance with the third embodiment.

In a time period from T1 to T2 excluding a readout time of the image sensor, the illumination light control circuit 150 causes the light sources LDa to LDe to emit light. Light emitted from the light sources LDa and LDb is detected by the B pixel, light emitted from the light source LDc is detected by the G pixel, and light emitted from the light sources LDd and LDe is detected by the R pixel. Thus obtained is a white light image to be displayed on the display section 300. If the brightness of the portion of interest in the white light image is determined as appropriate in step S5 in FIG. 7, the illumination light control circuit 150 turns off the light sources LDa to LDe during T2 to T1'.

In a time period from T1' to T2' excluding a readout time of the image sensor, the illumination light control circuit 150 causes the light sources LDa to LDe to emit light. Thus obtained is a white light image to be displayed on the display section 300. If the brightness of the portion of interest in the white light image is determined as not appropriate in step S5 in FIG. 7, the illumination light control circuit 150 causes the light sources LDa to LDe to emit light during T2' to T1".

A light quantity at this time is a light quantity for acquiring the support image. The first processing circuit 110 outputs the acquired support image to the diagnosis support section 121. Thereafter, the same operations as those during T1' to T1" are repeated until the first processing circuit 110 determines not to continue the observation in step S10 of FIG. 7.

Regarding FIG. 8, the present embodiment doubles an imaging frame rate without changing a display rate of moving images when executing steps S7 to S10. The display rate of moving images is an update rate of moving images, i.e., a rate of capturing display images. This example can smoothen the movement of moving images. Alternatively, when executing steps S7 to S10, the present embodiment may halve the display rate of images without changing the imaging frame rate. This example can simplify the system of imaging and illumination light control.

In accordance with the above-described embodiment, the endoscope apparatus 10 includes: the imaging section that captures an image of the object; the light source section 140 that emits illumination light onto the object; the illumination light control circuit 150 that controls illumination light; and the first processing circuit 110. The illumination light control circuit 150 causes the light source section 140 to emit first illumination light in a first time period. The first processing circuit 110 generates a first image on the basis of image signals obtained with the first illumination light. The illumination light control circuit 150 causes the light source section 140 to emit second illumination light in a second time period on the basis of diagnosis support information extracted from the first image by the second processing circuit. The first processing circuit 110 generates a second image on the basis of image signals obtained with the second illumination light. The first processing circuit 110 acquires diagnosis support information re-extracted by the second processing circuit 120 on the basis of the second image. The first processing circuit 110 performs image processing on a display image on the basis of the re-extracted diagnosis support information.

In FIG. 8, the first time period corresponds to the time period from T1' to T2'. The second time period corresponds to the time period from T2' to T1". The first illumination light corresponds to light emitted from the light sources LDa to LDe in the time period from T1' to T2'. The second illumination light corresponds to light emitted from the light sources LDa to LDe in the time period from T2' to T1".

The present embodiment performs feedback control of illumination light control on the basis of the diagnosis support information. The present embodiment can thus capture an image with illumination light appropriate for extracting the diagnosis support information. The present embodiment re-extracts the diagnosis support information on the basis of the thus acquired image, and can thereby extract the diagnosis support information more accurately.

Furthermore, in the present embodiment, the first processing circuit 110 outputs the first image to the display section 300 as the display image.

That is, the second image is an image acquired aside from the display image, and is not to be displayed. Accordingly, the illumination light control for the support image is independent of the illumination light control for the display image. By performing the illumination light control for the support image independently, the present embodiment enables appropriate illumination light control for the support image without affecting display quality. Although the present embodiment relies on the first processing circuit 110 in determining whether or not to continue the observation, this is not a limitative example. Instead, the illumination light control circuit 150 may determine whether or not to continue the observation, or an observation continuation necessity determination section or the like may be separately provided to determine whether or not to continue the observation.

5. Fourth Embodiment

In a fourth embodiment, the endoscope apparatus 10 sequentially acquires images having different degrees of brightness when capturing the images. When a portion of interest is extracted, the endoscope apparatus 10 extracts an image having optimum brightness or nearly-optimum brightness of the portion of interest, and re-extracts the portion of interest or makes a detailed classification of the portion of interest on the basis of the extracted image. Thus, the present embodiment does not need to change basic operations of the system, and only requires the diagnosis support section 121 to change operations on detection of the portion of interest, thereby simplifying and speeding up the operations.

Specifically, the illumination light control circuit 150 causes the light sources LDa to LDe to emit light in first to k-th light quantities, and the imaging unit 213 captures images of the object in the respective light quantities, where k is an integer of two or greater. The first processing circuit 110 acquires first to k-th candidate images corresponding to the respective first to k-th light quantities. Taking brightness of an image set in a normal observation mode as a center value, the first to k-th candidate images include an image with the center value, one or more images darker than the image with the center value, and one or more images brighter than the image with the center value. Note that the brightness of the image higher than the center value and the brightness of the image lower than the center value may be set on the basis of brightness of a bright portion or dark portion of the image in the normal observation mode. Alternatively, the brightness of the image higher than the center value and the brightness of the image lower than the center value may be set in accordance with a predetermined value. The predetermined value may be changed, for example, on the basis of an observation area of an internal organ.

The first processing circuit 110 outputs the image with the center value to the display section 300 as a display image. In addition, the first processing circuit 110 outputs the first to k-th candidate images to the diagnosis support section 121. The diagnosis support section 121 extracts diagnosis support information from the image with the center value. When a portion of interest is detected in the image with the center value, the diagnosis support section 121 selects an image having appropriate brightness of the detected portion of interest from the first to k-th candidate images. The diagnosis support section 121 re-extracts diagnosis support information regarding the portion of interest on the basis of the selected image.

In accordance with the above-described embodiment, the light source section 140 emits first to k-th illumination light having different light quantities onto the object. The first processing circuit 110 acquires the first to k-th candidate images corresponding to the respective first to k-th illumination light on the basis of image signals from the imaging section. The first processing circuit 110 generates a display image on the basis of the first to k-th candidate images, and also outputs the first to k-th candidate images to the second processing circuit 120. The second processing circuit 120 extracts diagnosis support information on the basis of the image selected from the first to k-th candidate images. The second processing circuit 120 then re-selects an image from the first to k-th candidate images on the basis of the diagnosis support information.

Furthermore, in the present embodiment, the second processing circuit 120 re-extracts diagnosis support information on the basis of the re-selected image. The first processing circuit 110 performs image processing on the display image on the basis of the diagnosis support information re-extracted by the second processing circuit 120.

The present embodiment performs feedback control on the basis of the diagnosis support information when selecting an image from the plurality of candidate images. The present embodiment can thus acquire an image having appropriate brightness for extracting the diagnosis support information. Then, the present embodiment re-extracts the diagnosis support information on the basis of the thus acquired image, and can thereby extract the diagnosis support information more accurately. In addition, this feedback control is performed independently of the dimming control for the display image. Hence, the present embodiment can provide an image whose brightness makes the image easily viewable by the operator, and can add more accurate support display information to this image. Further, the feedback control, which is performed by the second processing circuit 120, does not need to change a conventional dimming system or the like.

Furthermore, in the present embodiment, the light source section 140 emits first to m-th light having different colors. At this time, the light source section 140 may emit the first to k-th illumination light, with light quantities of all of the first to m-th light being different from one another, or the light source section 140 may emit the first to k-th illumination light, with light quantities of part of the first to m-th light being different from one another. For example, in a case where the diagnosis support section 121 extracts the diagnosis support information from the V image and the G image, the illumination light control circuit 150 may differentiate light quantities of the light sources LDa and LDc.

6. Fifth Embodiment

In a fifth embodiment, the endoscope apparatus 10 switches a wavelength or light quantity ratio of illumination light in accordance with an extracted lesion. This is expected to increase a certainty of diagnosis support information.

In a case where the object is a living body, there is a known relationship between a type of the portion of interest and a wavelength or light quantity ratio of illumination light appropriate for observing the portion of interest. In the present embodiment, the endoscope apparatus 10 automatically switches the wavelength or light quantity ratio of illumination light in accordance with the type of the portion of interest.

For example, in a case where the diagnosis support section 121 detects a suspected cancer in an image, the illumination light control circuit 150 causes the light source section 140 to emit purple light and green light by switching wavelengths of illumination light in accordance with absorption characteristics of hemoglobin. The illumination light control circuit 150 changes light quantities of the purple light and green light approximately to a ratio of 10:1 to 2:1. That is, the illumination light control circuit 150 changes a light quantity ratio such that the purple light quantity is higher than the green light quantity. A resulting image shows blood vessels with a higher contrast, thereby increasing a degree of certainty of information about a cancer, such as a type, degree of progression, degree of invasiveness, etc., detected by the AI.

For example, in a case where indocyanine green (ICG) is injected intravenously, the illumination light control circuit 150 causes the light source section 140 to emit near-infrared light. In this case, the light source section 140 further includes a light source that emits the near-infrared light. The near-infrared light has a wavelength of about 800 nm±20 nm. The image sensor acquires an image captured with infrared light on a somewhat longer wavelength side of illumination light. This enables acquisition of an image captured with fluorescence excited by illumination light and emitted from the ICG, thereby increasing a degree of certainty of a region, boundary, etc. of a lesion extracted by the AI.

For example, the illumination light control circuit 150 may also control the wavelength or light quantity ratio of illumination light in accordance with a feature substance present in the portion of interest. For example, the feature substance is hemoglobin, carotene, ICG, or the like.

In addition, in a case of a suspected cancer, the illumination light control circuit 150 switches illumination light to a special light mode such as an NBI mode or the like. This enables acquisition of a special light image, thereby increasing a degree of certainty of classification of the lesion and also enabling usage of a result program of machine learning using the NBI image or the like.

It is also preferable to emit illumination light before the adjustment and illumination light after the adjustment alternately. In this situation, the display image may be replaced with an image after the adjustment, or may remain an image before the adjustment. In the former case, the display image can have higher viewability of the portion of interest. In the latter case, the display image does not change during observation and remains easily viewable.

Figure 9:
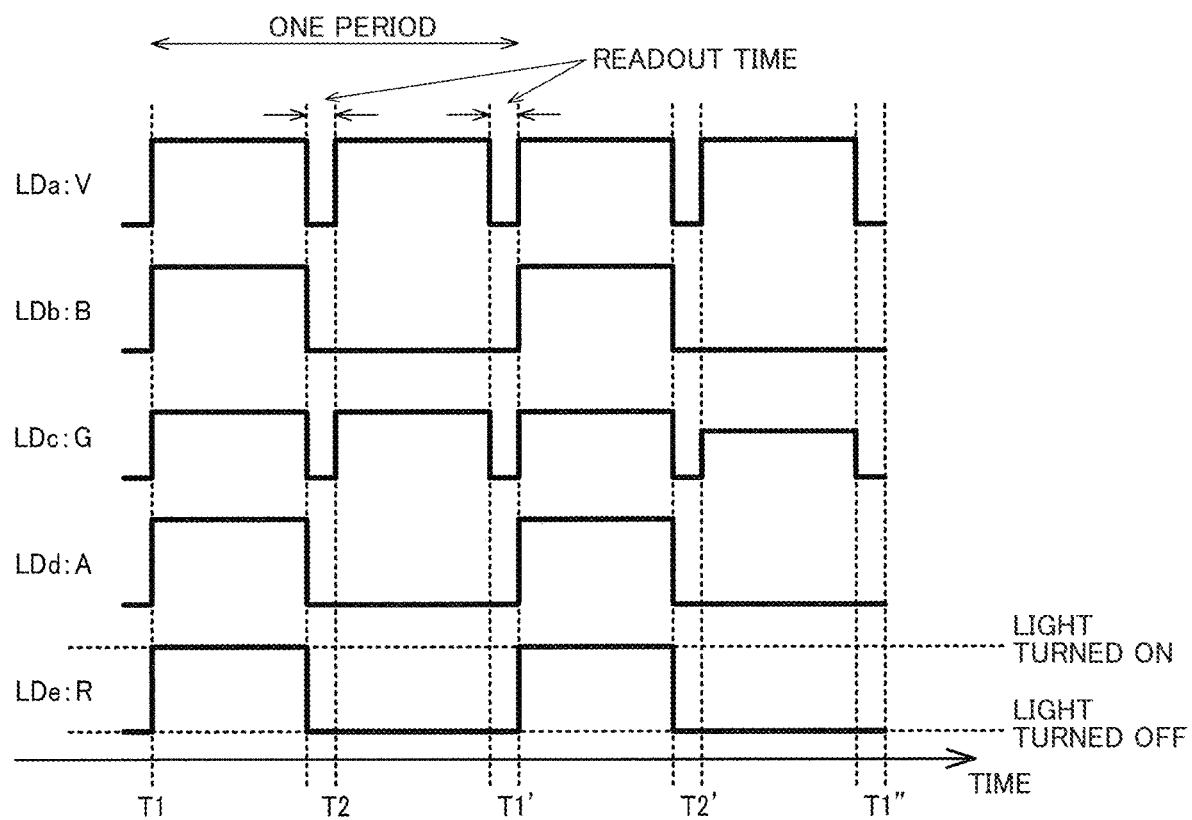
FIG. 9 illustrates a first example of a light emission sequence in accordance with a fifth embodiment.

FIG. 9 illustrates a first example of an emission sequence in accordance with the fifth embodiment. In a time period from T1 to T2 excluding a readout time of the image sensor, the illumination light control circuit 150 causes the light sources LDa to LDe to emit light. Thus obtained is a white light image to be displayed on the display section 300. In a time period from T2 to T1' excluding a readout time of the image sensor, the illumination light control circuit 150 causes the light sources LDa and LDc to emit light. For example, a light quantity ratio of LDa and LDc is 1:1. Thus obtained is a support image. The diagnosis support section 121 extracts diagnosis support information from the support image, and outputs the diagnosis support information to the illumination light control circuit 150. At this time, assume that the diagnosis support information indicates a suspected cancer.

In a time period from T1' to T2' excluding a readout time of the image sensor, the illumination light control circuit 150 causes the light sources LDa to LDe to emit light. Thus obtained is a white light image to be displayed on the display section 300. In a time period from T2' to T1" excluding a readout time of the image sensor, the illumination light control circuit 150 causes the light sources LDa and LDc to emit light. For example, a light quantity ratio of LDa and LDc is between 10:1 and 2:1. Thus obtained is a support image, from which the diagnosis support section 121 re-extracts diagnosis support information regarding the portion of interest.

Figure 10:
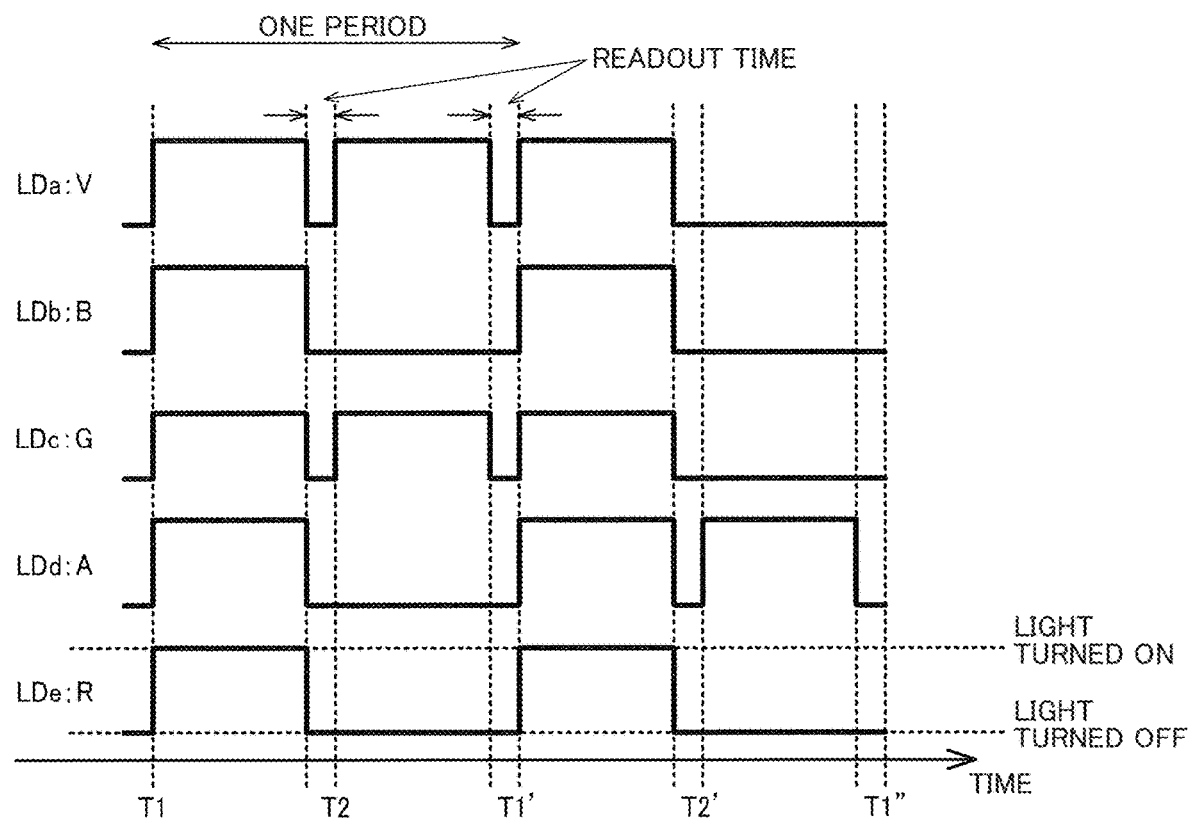
FIG. 10 illustrates a second example of the light emission sequence in accordance with the fifth embodiment.

FIG. 10 illustrates a second example of the emission sequence in accordance with the fifth embodiment. In a time period from T1 to T2 excluding a readout time of the image sensor, the illumination light control circuit 150 causes the light sources LDa to LDe to emit light. Thus obtained is a white light image to be displayed on the display section 300. In a time period from T2 to T1' excluding a readout time of the image sensor, the illumination light control circuit 150 causes the light sources LDa and LDc to emit light. Thus obtained is a support image. The diagnosis support section 121 extracts diagnosis support information from the support image, and outputs the diagnosis support information to the illumination light control circuit 150. At this time, assume that the diagnosis support information identifies the portion of interest as a lesion, and that appropriate light for analyzing the lesion is, for example, orange light.

In a time period from T1' to T2' excluding a readout time of the image sensor, the illumination light control circuit 150 causes the light sources LDa to LDe to emit light. Thus obtained is a white light image to be displayed on the display section 300. In a time period from T2' to T1" excluding a readout time of the image sensor, the illumination light control circuit 150 causes the light source LDd to emit light. Thus obtained is a support image, from which the diagnosis support section 121 re-extracts diagnosis support information regarding the portion of interest.

In accordance with the above-described embodiment, the illumination light control circuit 150 controls at least one of the light quantity, wavelength, and light quantity ratio of the support illumination light on the basis of the diagnosis support information. Note that the example of controlling the light quantity is described in the first embodiment. The illumination light control circuit 150 may control only any one of the light quantity, the wavelength, and the light quantity ratio, any two of the light quantity, the wavelength, and the light quantity ratio, or all of the light quantity, the wavelength, and the light quantity ratio.

The present embodiment performs feedback control of at least one of the light quantity, wavelength, and light quantity ratio of illumination light on the basis of the diagnosis support information, thereby enabling acquisition of illumination light optimum for re-extracting the diagnosis support information.

Furthermore, in the present embodiment, the light source section 140 emits the first to m-th light having different colors as illumination light, where m is an integer of two or greater. In the case of controlling the light quantity, the illumination light control circuit 150 controls the light quantity of light serving as the support illumination light out of the first to m-th light on the basis of the diagnosis support information. In the case of controlling the wavelength, the illumination light control circuit 150 selects one or more kinds of light from the first to m-th light as the support illumination light on the basis of the diagnosis support information. In the case of controlling the light quantity ratio, the illumination light control circuit 150 controls the light quantity ratio of more than one kind of light serving as the support illumination light out of the first to m-th light on the basis of the diagnosis support information.

In the configuration example of FIG. 1, m=5, and the first to m-th light is five kinds of light emitted from the light sources LDa to LDe. For example, in FIG. 4, the support illumination light is light emitted from the light sources LDa and LDc between T2 and T1'. The illumination light control circuit 150 controls light quantities of these kinds of light on the basis of the diagnosis support information. Alternatively, in FIG. 10, the support illumination light between T2' and T1" is light emitted from the light source LDd. The illumination light control circuit 150 selects this light on the basis of the diagnosis support information. Alternatively, in FIG. 9, the support illumination light between T2' and T1" is light emitted from the light sources LDa and LDc. The illumination light control circuit 150 controls a light quantity ratio of these kinds of light on the basis of the diagnosis support information.

The present embodiment can control these kinds of light independently by using the first to m-th light having different colors as illumination light. Independent control of these kinds of light enables control of at least one of the light quantity, wavelength, light quantity ratio of illumination light.

Furthermore, in the present embodiment, the diagnosis support information includes type information about the portion of interest included in the object. The illumination light control circuit 150 controls the wavelength, light quantity, and light quantity ratio of the support illumination light on the basis of the type information. The type of the portion of interest corresponds to, for example, a lesion, hemorrhage, inflammation, or the like. Alternatively, in a case where the portion of interest is the lesion, the type of the portion of interest is a type of the lesion, such as a polyp or a cancer.

As described above, there is a known relationship between the type of the portion of interest and the wavelength or light quantity ratio of illumination light appropriate for observing the portion of interest. The present embodiment enables selection of an appropriate wavelength or light quantity ratio of illumination light in accordance with the type of the portion of interest. Alternatively, the present embodiment enables selection of an appropriate light quantity in accordance with the type of the portion of interest. The present embodiment can thus re-extract the diagnosis support information regarding the portion of interest on the basis of an image captured with illumination light having the appropriate wavelength, light quantity, or light quantity ratio.

7. Details of Diagnosis Support Section and Diagnosis Support Method

Processing performed by the diagnosis support section 121 will be described below. While a description is given of an example in a case where support images are the V and G images, the support images are not limited thereto.

The diagnosis support section 121 generates diagnosis support information by the AI processing on the basis of the V and G images that can show blood vessels with a high contrast. The present embodiment selects images having wavelengths that enable detection of hemoglobin, i.e., blood vessels, with a high contrast, thereby generating the diagnosis support information on the basis of a pattern or distribution of the blood vessels. For example, a cancer can be assumed as the portion of interest.

For the AI processing, the V and G images are input as individual images. That is, the diagnosis support section 121 extracts a portion of interest from each of the V and G images. If there is a portion of interest, the diagnosis support section 121 generates the diagnosis support information regarding the portion of interest. If the portion of interest has been extracted, the diagnosis support section 121 causes a memory, which is not illustrated, to store the position, contour, etc. of the portion of interest. The diagnosis support section 121 causes the memory to store this information with respect to each of the V and G images. The diagnosis support section 121 estimates whether or not the extracted portion of interest is a cancer. If the portion of interest is a cancer, the diagnosis support section 121 estimates a degree of progression, stage level or other like information about the cancer. The diagnosis support section 121 outputs estimated results as the diagnosis support information. The diagnosis support information can be generated by a commonly used or available AI technology. In the case of using machine learning, various publicly-known technologies can be used for preparation, selection, and the like of teacher data. Note that the input to the AI processing may be a combined image of the V and G images.

As the diagnosis support information, the following information can be assumed as examples. A piece of information or a combination of more than one piece of information out of the following information can be adopted as the diagnosis support information.

(1) Location information: Position, shape, and contour of the portion of interest. The contour includes a demarcation line that separates between the cancer and normal cells.

(2) Form information: Is the portion of interest convex, flat, or concave? Is the portion of interest pedunculated or not?

(3) Status information: Is the portion of interest dispersed or located in one place? In a case where the portion of interest is dispersed, the concentration of the portion of interest, the size of each portion of interest, or the like.

(4) Other information: Presence/absence of hemorrhage, trace of treatment, trace of surgery, treatment for eradication of *Helicobacter pylori*, and other like information.

The diagnosis support information may be pieces of information (1) to (4) themselves, or may be comprehensive evaluation of these pieces of information. For example, the information (5) and (6) below may be used as the diagnosis support information.

(5) Medical feature information: Does the portion of interest correspond to a cancer? In a case of a cancer, benignancy or malignancy of the cancer, or the stage (from I to IV) of the cancer.

(6) Treatment information: information about a treatment method appropriate for the portion of interest, a surgical method appropriate for the portion of interest, medication appropriate for the portion of interest, or other like information.

For example, data that associates information (1) to (6) with image information may be used as teacher data, so that the information (1) to (6) can be output as the result of the AI processing.

Alternatively, the diagnosis support section 121 may perform the AI processing as first processing, and may further perform subsequent second processing. In this case, the data that associates the information (1) to (4) with the image information as teacher data in the AI processing. The AI processing provides the information (1) to (4) as an output. The second processing generates the information (5) and (6) on the basis of the information (1) to (4) output by the AI processing. The second processing is implemented by a program that has been created following a method conducted by doctors on the basis of the information (1) to (4).

As described in the first to fifth embodiments, the diagnosis support section 121 re-extracts the diagnosis support information on the basis of an image re-acquired by the dimming control or the like. For example, the diagnosis support section 121 performs a first phase analysis to determine whether or not a portion of interest is present in an image, and extracts position information about the portion of interest as the diagnosis support information. The diagnosis support section 121 performs a second phase analysis on the basis of an image re-acquired on the basis of the diagnosis support information. The diagnosis support section 121 extracts the information (1) to (6) in the second phase analysis, and outputs the diagnosis support information to the first processing circuit 110.

Now, a method of presenting the diagnosis support information to the operator is described.

The first processing circuit 110 performs image processing on a display image on the basis of diagnosis support information to display support display information corresponding to the diagnosis support information.

For example, the first processing circuit 110 superimposes the support display information indicating a position or a contour on the display image, on the basis of the diagnosis support information regarding the position or the contour. For example, the first embodiment acquires six images at substantially the same time. Each image is captured at substantially the same position and angle. Thus, information regarding the position and contour of the portion of interest extracted from one of these images indicates substantially the same position and contour in the other images. Consequently, it is possible to omit a process of calculating a positional relationship among these images and aligning the positions of the portions of interest in these images by computation. As a matter of course, position information among images may be computed by a publicly-known technology such that the positions and contours of the portions of interest in these images indicate the same portion.

Information except the position and contour may be displayed in a region in a region in which an object image is displayed on a screen of the display section 300. Alternatively, the information may be superimposed on the object image. Various other publicly-known display methods may be adopted.

8. Endoscope System

While the endoscope apparatus 10 includes the second processing circuit 120 in FIG. 1, the second processing circuit 120 may be arranged outside the endoscope apparatus 10. A system configuration example in this case will be described below.

Figure 11:
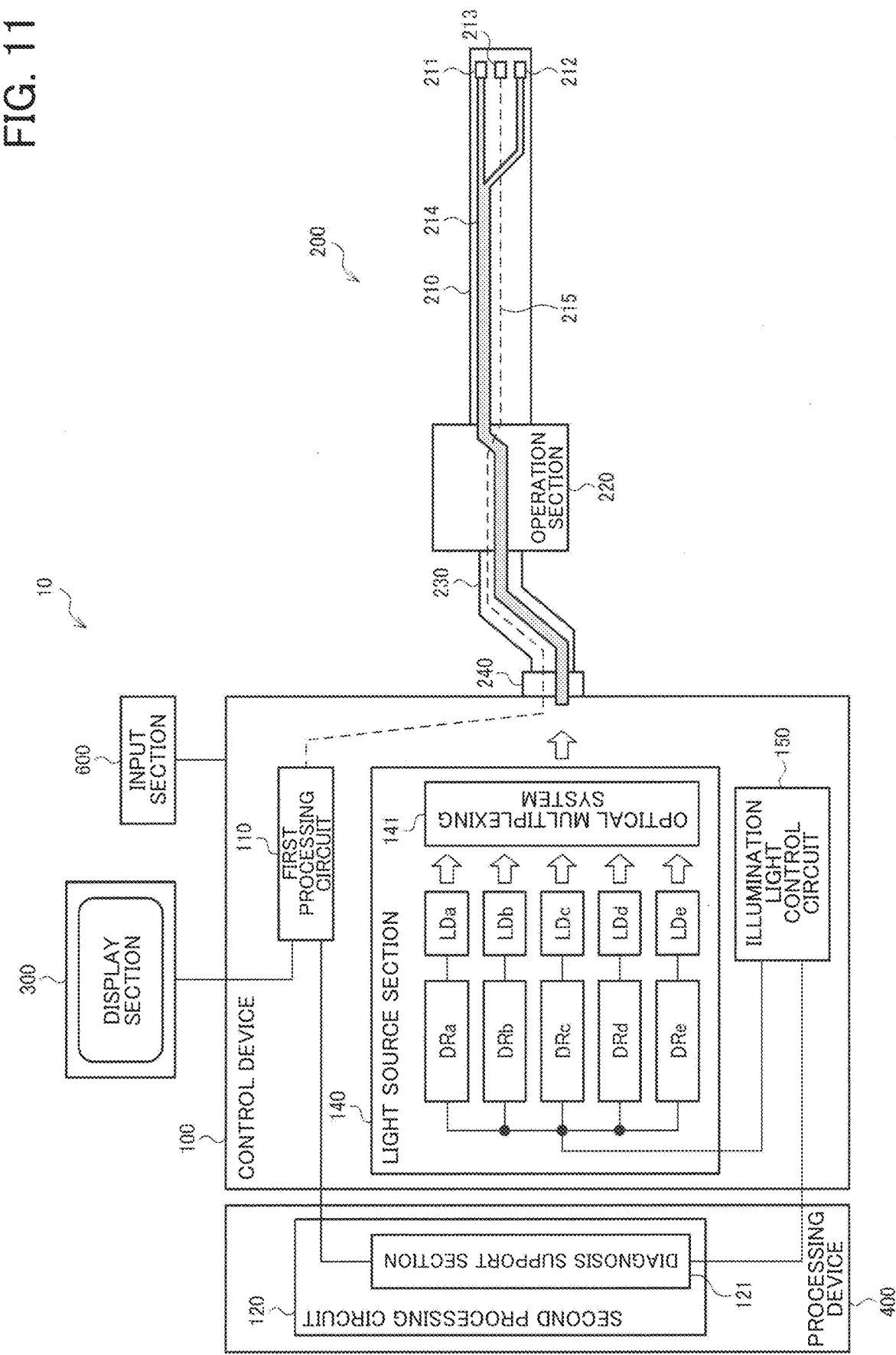
FIG. 11 illustrates a configuration example of an endoscope system.

FIG. 11 illustrates a configuration example of an endoscope system. The endoscope system includes the endoscope apparatus 10 and a processing device 400. In FIG. 11, the processing device 400 arranged separately from the endoscope apparatus 10 includes the second processing circuit 120. The processing device 400 is, for example, an information processing device such as a personal computer (PC) and a server. In addition, the processing device 400 is not limited to one information processing device, and may be, for example, a cloud processing system connected to a network.

The control device 100 of the endoscope apparatus 10 includes an interface, which is not illustrated, to communicate images and diagnosis support information. Various kinds of inter-device interface can be adopted as this interface. For example, the interface may be a wired communication interface such as a universal serial bus (USB) and a local area network (LAN), or may be a wireless communication interface such as a wireless LAN.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
an imaging sensor configured to capture an image of an object;
a light source; and
one or more processors comprising hardware, wherein the one or more processors are configured to:
cause the light source to emit display illumination light;
acquire a display image captured by the imaging sensor based on an image signal obtained with the display illumination light;
cause the light source to emit first support illumination light in a first time period;
acquire a first support image captured by the imaging sensor based on an image signal obtained with the first support illumination light;
extract first diagnosis support information to be used for dimming control, based on the first support image;
cause the light source device to emit second support illumination light in a second time period, the second support illumination light resulting from the dimming control using the first diagnosis support information;
acquire a second support image based on an image signal obtained with the second support illumination light;
acquire second diagnosis support information as support display information based on the second support image; and
execute image processing, based on the second diagnosis support information, on the display image, and output a processed display image to a display.

2. The endoscope apparatus as defined in claim 1, wherein the one or more processors are configured to:
extract information about a portion of interest as the first diagnosis support information based on the first support image; and
extract the second diagnosis support information regarding the portion of interest based on the information about the portion of interest and the second support image.

3. The endoscope apparatus as defined in claim 1, wherein the one or more processors are configured to, in performing the dimming control, control at least one of a light quantity, a wavelength, and a light quantity ratio of the second support illumination light based on the first diagnosis support information.

4. The endoscope apparatus as defined in claim 3,
wherein the first support illumination light and the second support illumination light include first to m-th light having different colors, where m is an integer of two or greater, and
wherein the one or more processors are configured to:
in a case of controlling the light quantity, control the light quantity of light serving as the second support illumination light out of the first to m-th light on the basis of the first diagnosis support information;

in a case of controlling the wavelength, selects one or more kinds of light from the first to m-th light as the second support illumination light based on the first diagnosis support information; and in a case of controlling the light quantity ratio, controls the light quantity ratio between more than one kind of light serving as the second support illumination light out of the first to m-th light based on the first diagnosis support information.

5. The endoscope apparatus as defined in claim 1,
wherein the first diagnosis support information includes information about a portion of interest included in the object, and
wherein the one or more processors are configured to control a light quantity of the second support illumination light based on brightness information about an image of the portion of interest included in the first support image.

6. The endoscope apparatus as defined in claim 5,
wherein the first diagnosis support information includes position information about the portion of interest and brightness information about the image of the portion of interest as the information about the portion of interest, and
wherein the one or more processors are configured to control the light quantity of the second support illumination light based on the first diagnosis support information.

7. The endoscope apparatus as defined in claim 1,
wherein the first diagnosis support information includes type information about a portion of interest included in the object, and
wherein the one or more processors are configured to control a wavelength, a light quantity, or a light quantity ratio of the second support illumination light based on the type information.

8. The endoscope apparatus as defined in claim 1, wherein the one or more processors are configured to control a light quantity of the display illumination light based on the display image.

9. An operating method of an endoscope apparatus, the operating method comprising:
causing a light source to emit display illumination light;
acquiring a display image captured by an imaging sensor based on an image signal obtained with the display illumination light;
causing the light source to emit first support illumination light in a first time period;
acquiring a first support image captured by the imaging sensor based on an image signal obtained with the first support illumination light;
extracting first diagnosis support information to be used for dimming control, based on the first support image;
cause the light source to emit second support illumination light in a second time period, the second support illumination light resulting from the dimming control using the first diagnosis support information;
acquiring a second support image based on an image signal obtained with the second support illumination light;
acquiring second diagnosis support information as support display information based on the second support image; and
execute image processing, based on the second diagnosis support information, on the display image, and outputting a processed display image to a display.

10. The operating method as defined in claim 9, further comprising:
extracting information about a portion of interest as the first diagnosis support information based on the first support image; and
extracting the second diagnosis support information regarding the portion of interest based on the information about the portion of interest and the second support image.

11. The operating method as defined in claim 9, wherein performing the dimming control comprises controlling at least one of a light quantity, a wavelength, and a light quantity ratio of the second support illumination light based on the first diagnosis support information.

12. The operating method as defined in claim 11,
wherein the first support illumination light and the second support illumination light include first to m-th light having different colors, where m is an integer of two or greater,
wherein controlling the light quantity comprises controlling the light quantity of light serving as the second support illumination light out of the first to m-th light on the basis of the first diagnosis support information,
wherein controlling the wavelength comprises selecting one or more kinds of light from the first to m-th light as the second support illumination light based on the first diagnosis support information, and
wherein controlling the light quantity ratio comprises controlling the light quantity ratio between more than one kind of light serving as the second support illumination light out of the first to m-th light based on the first diagnosis support information.

13. The operating method as defined in claim 9,
wherein the first diagnosis support information includes information about a portion of interest included in the object, and
wherein the operating method further comprises controlling a light quantity of the second support illumination light based on brightness information about an image of the portion of interest included in the first support image.

14. The operating method as defined in claim 13,
wherein the first diagnosis support information includes position information about the portion of interest and brightness information about the image of the portion of interest as the information about the portion of interest, and
wherein the operating method further comprises controlling a light quantity of the second support illumination light based on the first diagnosis support information.

15. The operating method as defined in claim 9,
wherein the first diagnosis support information includes type information about a portion of interest included in the object, and
wherein the operating method further comprises controlling a wavelength, a light quantity, or a light quantity ratio of the second support illumination light based on the type information.

16. The operating method as defined in claim 9, further comprising controlling a light quantity of the display illumination light based on the display image.

17. A non-transitory information storage medium storing a program, the program causing a computer to at least execute:
causing a light source to emit display illumination light;

acquiring a display image captured by an imaging sensor based on an image signal obtained with the display illumination light;
causing the light source to emit first support illumination light in a first time period;
acquiring a first support image captured by the imaging sensor based on an image signal obtained with the first support illumination light;
extracting first diagnosis support information to be used for dimming control, based on the first support image;
cause the light source to emit second support illumination light in a second time period, the second support illumination light resulting from the dimming control using the first diagnosis support information;
acquiring a second support image based on an image signal obtained with the second support illumination light;
acquiring second diagnosis support information as support display information based on the second support image; and
executing image processing, based on the second diagnosis support information, on the display image, and outputting a processed display image to a display.

18. A non-transitory information storage medium as defined in claim 17, wherein the program further causes the computer to execute:
extracting information about a portion of interest as the first diagnosis support information based on the first support image; and
extracting the second diagnosis support information regarding the portion of interest based on the information about the portion of interest and the second support image.

\* \* \* \* \*